US005859338A

United States Patent [19]

Meyerowitz et al.

[11] Patent Number: 5,859,338

[45] Date of Patent: Jan. 12, 1999

[54] PLANT CLAVATA1 NUCLEIC ACIDS, TRANSFORMED PLANTS, AND PROTEINS

[75] Inventors: Elliot M. Meyerowitz, Pasadena, Calif.; Steven E. Clark, Ann Arbor, Mich.; Robert W. Williams, Pasadena, Calif.

[73] Assignee: California Institute of Technology, Pasadena, Calif.

[21] Appl. No.: 473,553

[22] Filed: Jun. 6, 1995

[51] Int. Cl.[6] .......................... C12N 15/29; C12N 15/82; C12N 5/04; A01H 5/00

[52] U.S. Cl. ........................ 800/205; 536/23.6; 435/69.1; 435/172.3; 435/320.1; 435/419

[58] Field of Search ................................ 536/23.6, 24.1; 435/69.1, 172.3, 320.1, 419; 800/205

[56] References Cited

FOREIGN PATENT DOCUMENTS

| | | |
|---|---|---|
| WO 9008826 | 8/1990 | WIPO . |
| WO 9008827 | 8/1990 | WIPO . |
| WO 9301294 | 1/1993 | WIPO . |
| WO 9321334 | 10/1993 | WIPO . |

OTHER PUBLICATIONS

Chang, C., et al., "The TMK1 Gene from Arabidopsis Codes for a Protein with Structural and Biochemical Characteristics of a Receptor Protein Kinase", *The Plant Cell*, 4:1263–1271 (1992).

Bowman, J. L., et al., "*Arabidopsis Thaliana*: A Review", *Oxford Surveys of Plant Molecular & Cell Biology*, 5:57–87 (1988).

Crone, W., et al., "Flower Development in the Organ Number Mutant Clavatal–1 of *Arabidopsis Thaliana* (Brassicaceae)", *American Journal of Botany*, 80(12):1419–1426 (1993).

Haughn, G. W., et al., "Genetic Control of Morphogenesis in Arabidopsis", *Developmental Genetics*, 9:73–89 (1988).

Koornneef, M., et al., Linage map of *Arabidopsis thalana, The Journal of Heredity*, 74:265–272 (1983).

McKelvie, A. D., "A List of Mutant Genes in *Arabidopsis Thaliana* (L.) Heynh", *Radiation Botany*, 1:233–241 (1962).

Leyser, H. M. Ottoline, et al, Characterisation of three shoot apical meristem mutants of *Arabidopsis thaliana, Development*, 116:397–403 (1992).

Clark, S. E., et al., "CLAVATA1, a regulator of meristem and flower development in Arabidopsis", *Development*, 119:397–418 (1993).

Lewin, R. 1987. Science 237:1570.

Reeck et al. 1987. Cell 50:667.

*Primary Examiner*—David T. Fox
*Attorney, Agent, or Firm*—Flehr Hohbach Test Albritton & Herbert LLP; Richard F. Trecartin; Robin M. Silva

[57] ABSTRACT

The invention generally relates to clavata1 nucleic acids, proteins, and antibodies, and to plants transformed with clavata1 nucleic acids having altered phenotypes.

13 Claims, 15 Drawing Sheets

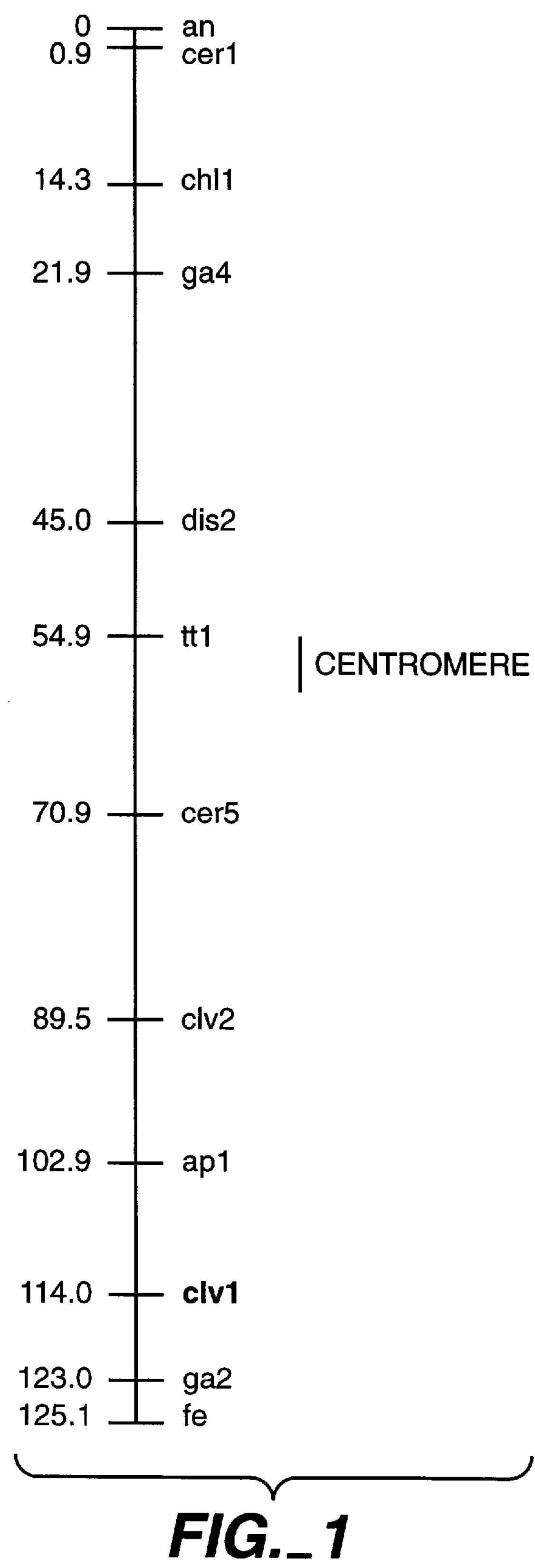
FIG._1

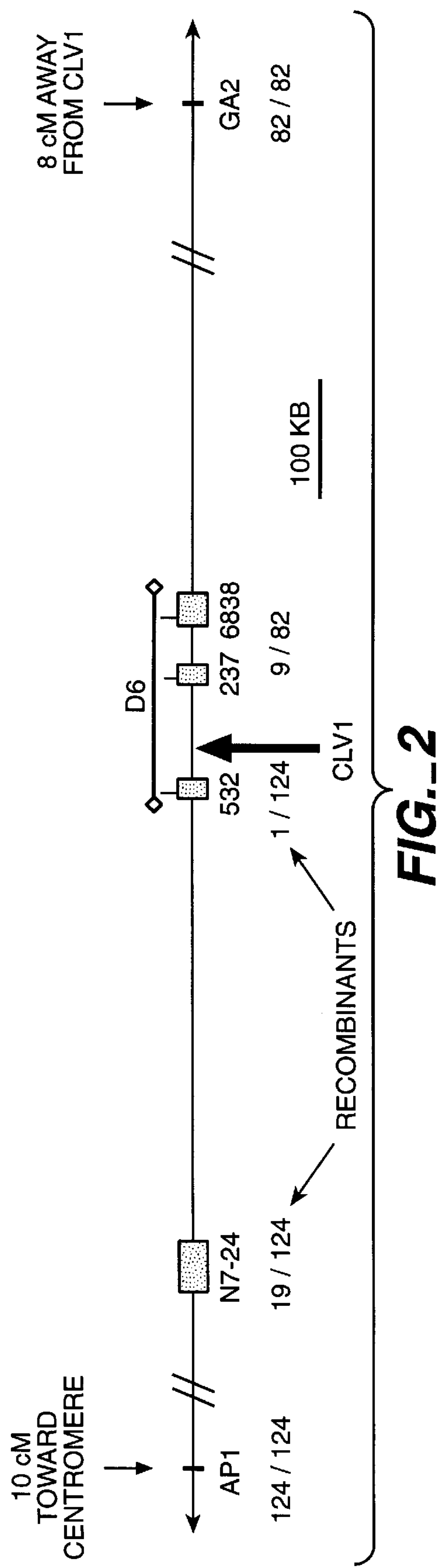
*FIG._2*
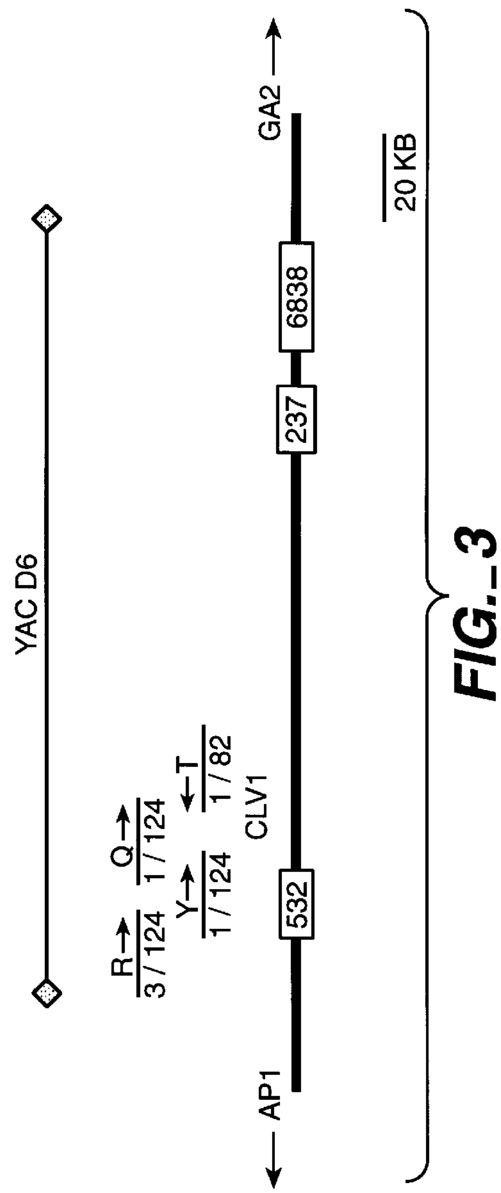
*FIG._3*

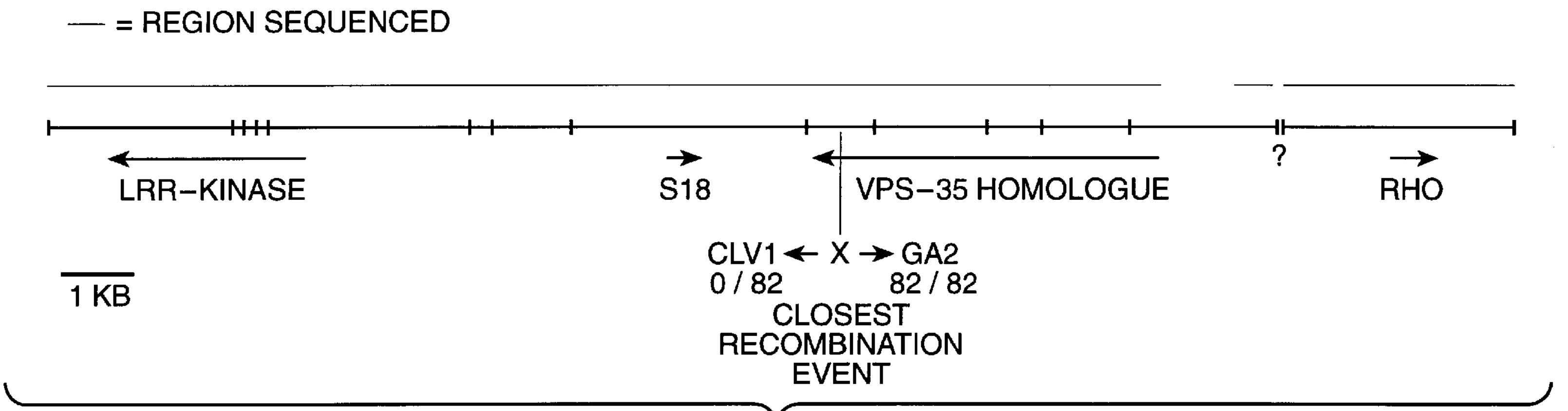
FIG._4
| ALLELE | BASE CHANGE | POSITION | AMINO ACID CHANGE | SEVERITY OF PHENOTYPE |
|---|---|---|---|---|
| *clv1-1* | G to A | 855 | G to D | INTERMEDIATE; SEMI-DOMINANT |
| *clv1-2* | G to A | 880 | G to E | WEAK |
| *clv1-4* | G to A | 200 | G to E | STRONG |
| *clv1-5* | G to A | 855 | G to D | INTERMEDIATE; SEMI-DOMINANT |
| *clv1-6* | ADDITIONAL A | 750 | FRAMESHIFT | WEAK |
| *clv1-8* | G to A | 294 | D to N | STRONG |
| *clv1-9* | C to T | 838 | A to V | WEAK |
FIG._7

```
5'   TCT AGA AAT TGG TCC AAA GTT CTT TCA CCC GTG AGT CAT TTA GTG ATA AAG ATG
55   ACA TGA TTT TTG GTG ATA AAT TTT CCA TCG TTG CTA TAT GTC GTT ATA TTA TTC
109  TCC TAT ATG TAT ATT ATA CTA TTT ACA TCA GAA AAT AAT CCA AAG TTT AGA GAT
163  TCT TTT TTA CAA TAA TAA AAT TTC CCA CTT ACT AAA AAG AGC TCC TTT TCT GCT
217  GAA GAG AAC CTA AAC CTT TAT TCC CAA AGT TCA TTG AGT TAG AGC ATT TTC AGC
271  GAA TCA CAT AAG AGA TGC TCT CTT CTT CAT CAC TAA TTG ACA TCT CAT TGT TTT
325  AAA GGT TGC ACT TGT ACC TGT TGA TCT GAT TCT CAA TCC ACT TAA GTT AAA CCA
379  AAT AGA CAC GAG AAA AAA GCA CAT TTA TTT GTT GCT AAG TAT GCA TAT TTT TCA
433  GCG TTT ACT TCT TAA TCT AAT GTA TAT CAT AAG ATA ATA TCT AAA AGA GAA TGC
487  ACA AAA GAT TAT TAA TAT GAG AAA TTC GCT GCC ATT TAG GAA GGA CCT TTA TAC
541  CAA TAT ACC GCA ATA ATA ATA GAA CAT TGG TCC CCA AGT GTA TGT CAA CCC CAA
595  GTG TAT AGA TTT CTT TAA AGA TTA AAA TCC CTT TTT GTT GCT AAA GCA CCT GAT
649  ATA TTT TTC TAT CAA ACT AAA AAA ATT GTT AGC GGG ATG AAG ATA TAT TCG CCA
703  AGA ACC ATA GTG CTT GTA TAA CGG CAG ACC ATT AAT TCA CAA CTA TTA TTA TTT
757  TAT TGT TAG ATT GTT GAT AGA ATC GAT TTT GAT TGT GGC AGA ATC GAT CTT GTA
811  AAA ACT GCT TAA GGT GCT TAC TTA TAA TTA AGA AAG ATT CAC TTA TGT AAG TTA
865  AGC ATA TTA ATC ATA TCA TTC GGC CTA ATT CAT TAG GAA TAT TTT GCT ATT CGT
919  TTT GCC ATC ATT AAC AAC AAA ATT GAC ACG TTT TCA GCC AAA AGT ATT AAC AAC
973  TAA ACC TAA AAC TTC AAA CAT TAA ATA GTT TTT AGT ATC TTT AGT TTC AAA CTA
1027 GTG ATT TGT CCT AAT ATC AAC ACT ACG AAC GAA TTT ATA TAC ATT GAA CTT TTT
1081 TCT GAA TCA CCG ATT ACA AAA CGA ATA TAA TTT GGT ATC GGC AGT TGC TAT TAA
1135 TTT GAT CGG TTT GGA CTT TGG ACT AAT CAC GAT CAA ATC TTA AAT GGA CCG AAG
1189 TGA ATA AAT CCC TAA TGT TTT CAA GAG AGT CAC ACG AAC GAA ACA AAG GTA AAA
1243 TAT GAA CAT AGA GCG TGG GGA CTT GAA GCA GAA GGT CTG TAT GGT GAC ATA CCG
1297 GTG AGT GGA GTG TAT GAA TGA ACG AGA AGT GAG AAG ACA AAA TAC AAG AAA GAG
1351 CGT TGA CTT GGA AGT TAA AGC CAA AAA AAC CAC AAG GGG CAA ATT TGT CTC TTT
1405 AGG AAA AGG ACA CAG ACA GAC TTT CTA TAC GGG CCA ATT AGA AAA ATA GGC CCT
1459 ACT TCT AAT TAA AGC CCA TTT ACT TCT CTC CTT GTC TTC TTA TTC CTC TTT TCT
1513 CCC CAT CAC GTG ACG ACG ATG CTA TAA ACG CCG TCG ATT ATA TAA CTG GTG CCG
1567 TTG ACA GAC GGC GAC AGA AGA AAG AAA GAA GAA ACC ACA GGC TCT AGG GAA CGT
1621 AAC GTT ATG TCC TGT CTA TAG CAT TTA TAA CGG TCA GAT CAA CGC CGT TTA GAT
1675 AAA GAT CTG TCA ATG TTA AAG AAG AGA TGC ATC TCT ACA CCG TTA AAT TTA AAA
1729 CGC CGT GAA CCT CTT ATC TAT TGA TTT TTG TTT GAT GAA GCC AAA ACA AAT CGT
1783 GTC AGA AGA CTT ATC AGA GAA GAA GAA AAC GAC GAC GTT CCC GTT TCT CCA TGT
1837 CTA ATA AGT GTA GTA GTG GCG GCT ACT AAA AAC TCT AAA GTT TGA CTC CAG TAA
```

FIG._5A

```
1891 AAC TGC CTT TCT AGT GTA ATT CCA GTG ATT TTA GAG TTT GAA TAG TGT GTG ACC
1945 AAA TTT GAA AGT ACA ATC TCA GCA ATA TTA TTG ATC ACT CGT TAT AAA AGA ATC
1999 GAA TGT AAA AAT AGC CAA TGA GAG ACT GAG ACG TAT GTG TTT GAC CAT AAG TCG
2053 TAT AGT TTG TAT CTA TCT ACC TGC AAG ATC AGC AGA TGG TTC TCT GAT CAA TTG
2107 TAC CTT AAT TAT CTT TTA TTT TCG TAA AAT TTC TCT ATT CAC AAA TGA TAA ATC
2161 TAC TTA AGA CAG TAA CCA TAA CAA GAT TTA CAA GAT AAT TTG AAA AAT GAA CAC
2215 ATA AAA GTA TTT TGG CGC ATT ATT TTT AAT AAT AAC AAT ATT TAT GTA AAG TCA
2269 CAT AAA AGT ATA TAT TCG CTC ACA AAG TCT TAC GGT ATT TAG AAC AGT AGT ACC
2323 ACA TCG ATT CTC TTC ATC TTC TTC TTC ATA ATA TGC CAT TGT TCA TGT CTC TGT
2377 GTC CTA TCG CAT AAC ACT CAC GCT ATC TTA TTA TTT TCT CTC GCT CTT TCT CAC

2431 TGA GAG GAC ACT AAA AAA ATG GCG ATG AGA CTT TTG AAG ACT CAT CTT CTG TTT
     --- --- --- --- --- --- --- --- --- --- --- --- --- --- --- --- --- ---
      *   e   d   t   k   k   M   A   M   R   L   L   K   T   H   L   L   F

     CTG CAT CTG TAT CTA TTT TTC TCA CCA TGT TTC GCT TAC ACT GAC ATG GAA GTT
2485 --- --- --- --- --- --- --- --- --- --- --- --- --- --- --- --- --- ---
      L   H   L   Y   L   F   F   S   P   C   F   A   Y   T   D   M   E   V

2539 CTT CTC AAT CTC AAA TCC TCC ATG ATT GGT CCT AAA GGA CAC GGT CTC CAC GAC
     --- --- --- --- --- --- --- --- --- --- --- --- --- --- --- --- --- ---
      L   L   N   L   K   S   S   M   I   G   P   K   G   H   G   L   H   D

2593 TGG ATT CAC TCA TCT TCT CCG GAT GCT CAC TGT TCT TTC TCC GGC GTC TCA TGT
     --- --- --- --- --- --- --- --- --- --- --- --- --- --- --- --- --- ---
      W   I   H   S   S   S   P   D   A   H   C   S   F   S   G   V   S   C

2647 GAC GAC GAT GCT CGT GTT ATC TCT CTC AAC GTC TCC TTC ACT CCT TTG TTT GGT
     --- --- --- --- --- --- --- --- --- --- --- --- --- --- --- --- --- ---
      D   D   D   A   R   V   I   S   L   N   V   S   F   T   P   L   F   G

2701 ACA ATC TCA CCA GAG ATT GGG ATG TTG ACT CAT TTG GTG AAT CTA ACT TTA GCT
     --- --- --- --- --- --- --- --- --- --- --- --- --- --- --- --- --- ---
      T   I   S   P   E   I   G   M   L   T   H   L   V   N   L   T   L   A
```

FIG._5B

```
2755 GCC AAC AAC TTC ACC GGT GAA TTA CCA TTG GAG ATG AAG AGT CTA ACT TCT CTC
     --- --- --- --- --- --- --- --- --- --- --- --- --- --- --- --- --- ---
      A   N   N   F   T   G   E   L   P   L   E   M   K   S   L   T   S   L

2809 AAG GTT TTG AAT ATC TCC AAC AAT GGT AAC CTT ACT GGA ACA TTC CCT GGA GAG
     --- --- --- --- --- --- --- --- --- --- --- --- --- --- --- --- --- ---
      K   V   L   N   I   S   N   N   G   N   L   T   G   T   F   P   G   E

2863 ATT TTA AAA GCT ATG GTT GAT CTT GAA GTT CTT GAC ACT TAT AAC AAC AAT TTC
     --- --- --- --- --- --- --- --- --- --- --- --- --- --- --- --- --- ---
      I   L   K   A   M   V   D   L   E   V   L   D   T   Y   N   N   N   F

2917 AAC GGT AAG TTA CCA CCG GAG ATG TCA GAG CTT AAG AAG CTT AAA TAC CTC TCT
     --- --- --- --- --- --- --- --- --- --- --- --- --- --- --- --- --- ---
      N   G   K   L   P   P   E   M   S   E   L   K   K   L   K   Y   L   S

2971 TTC GGT GGA AAT TTC TTC AGC GGA GAG ATT CCA GAG AGT TAT GGA GAT ATT CAA
     --- --- --- --- --- --- --- --- --- --- --- --- --- --- --- --- --- ---
      F   G   G   N   F   F   S   G   E   I   P   E   S   Y   G   D   I   Q

3025 AGC TTA GAG TAT CTT GGT CTC AAC GGA GCT GGA CTC TCC GGT AAA TCT CCG GCG
     --- --- --- --- --- --- --- --- --- --- --- --- --- --- --- --- --- ---
      S   L   E   Y   L   G   L   N   G   A   G   L   S   G   K   S   P   A

3079 TTT CTT TCC CGC CTC AAG AAC TTA AGA GAA ATG TAT ATT GGC TAC TAC AAC AGC
     --- --- --- --- --- --- --- --- --- --- --- --- --- --- --- --- --- ---
      F   L   S   R   L   K   N   L   R   E   M   Y   I   G   Y   Y   N   S

3133 TAC ACC GGT GGT GTT CCA CGC GAG TTC GGT GGT TTA ACA AAG CTT GAG ATC CTC
     --- --- --- --- --- --- --- --- --- --- --- --- --- --- --- --- --- ---
      Y   T   G   G   V   P   R   E   F   G   G   L   T   K   L   E   I   L

3187 GAC ATG GCG AGC TGT ACA CTC ACC GGA GAG ATT CCG ACG AGT TTA AGT AAC CTG
     --- --- --- --- --- --- --- --- --- --- --- --- --- --- --- --- --- ---
      D   M   A   S   C   T   L   T   G   E   I   P   T   S   L   S   N   L
```

FIG._5C

```
3241 AAA CAT CTA CAT ACT CTG TTT CTT CAC ATC AAC AAC TTA ACC GGT CAT ATA CCA
     --- --- --- --- --- --- --- --- --- --- --- --- --- --- --- --- --- ---
      K   H   L   H   T   L   F   L   H   I   N   N   L   T   G   H   I   P

3295 CCG GAG CTT TCC GGT TTA GTC AGC TTG AAA TCT CTC GAT TTA TCA ATC AAT CAG
     --- --- --- --- --- --- --- --- --- --- --- --- --- --- --- --- --- ---
      P   E   L   S   G   L   V   S   L   K   S   L   D   L   S   I   N   Q

3349 TTA ACC GGA GAA ATC CCT CAA AGC TTC ATC AAT CTC GGA AAC ATT ACT CTA ATC
     --- --- --- --- --- --- --- --- --- --- --- --- --- --- --- --- --- ---
      L   T   G   E   I   P   Q   S   F   I   N   L   G   N   I   T   L   I

3403 AAT CTC TTC AGA AAC AAT CTC TAC GGA CAA ATA CCA GAG GCC ATC GGA GAA TTA
     --- --- --- --- --- --- --- --- --- --- --- --- --- --- --- --- --- ---
      N   L   F   R   N   N   L   Y   G   Q   I   P   E   A   I   G   E   L

3457 CCA AAA CTC GAA GTC TTC GAA GTA TGG GAG AAC AAT TTC ACG TTA CAA TTA CCG
     --- --- --- --- --- --- --- --- --- --- --- --- --- --- --- --- --- ---
      P   K   L   E   V   F   E   V   W   E   N   N   F   T   L   Q   L   P

3511 GCG AAT CTT GGC CGG AAC GGG AAT CTA ATA AAG CTT GAT GTC TCT GAT AAT CAT
     --- --- --- --- --- --- --- --- --- --- --- --- --- --- --- --- --- ---
      A   N   L   G   R   N   G   N   L   I   K   L   D   V   S   D   N   H

3565 CTC ACC GGA CTT ATC CCC AAG GAC TTA TGC AGA GGT GAG AAA TTA GAG ATG TTA
     --- --- --- --- --- --- --- --- --- --- --- --- --- --- --- --- --- ---
      L   T   G   L   I   P   K   D   L   C   R   G   E   K   L   E   M   L

3619 ATT CTC TCT AAC AAC TTC TTC TTT GGT CCA ATT CCA GAA GAG CTT GGT AAA TGC
     --- --- --- --- --- --- --- --- --- --- --- --- --- --- --- --- --- ---
      I   L   S   N   N   F   F   F   G   P   I   P   E   E   L   G   K   C

3673 AAA TCC TTA ACC AAA ATC AGA ATC GTT AAG AAT CTT CTC AAC GGC ACT GTT CCG
     --- --- --- --- --- --- --- --- --- --- --- --- --- --- --- --- --- ---
      K   S   L   T   K   I   R   I   V   K   N   L   L   N   G   T   V   P
```

FIG._5D

```
3727 GCG GGG CTT TTC AAT CTA CCG TTA GTT ACG ATT ATC GAA CTC ACT GAT AAT TTC
     --- --- --- --- --- --- --- --- --- --- --- --- --- --- --- --- --- ---
      A   G   L   F   N   L   P   L   V   T   I   I   E   L   T   D   N   F

3781 TTC TCC GGT GAA CTT CCG GTA ACG ATG TCC GGC GAT GTT CTC GAT CAG ATT TAC
     --- --- --- --- --- --- --- --- --- --- --- --- --- --- --- --- --- ---
      F   S   G   E   L   P   V   T   M   S   G   D   V   L   D   Q   I   Y

3835 CTC TCT AAC AAC TGG TTT TCC GGC GAG ATT CCA CCT GCG ATT GGT AAT TTC CCC
     --- --- --- --- --- --- --- --- --- --- --- --- --- --- --- --- --- ---
      L   S   N   N   W   F   S   G   E   I   P   P   A   I   G   N   F   P

3889 AAT CTA CAG ACT CTA TTC TTA GAT CGG AAC CGA TTT CGC GGC AAC ATT CCG AGA
     --- --- --- --- --- --- --- --- --- --- --- --- --- --- --- --- --- ---
      N   L   Q   T   L   F   L   D   R   N   R   F   R   G   N   I   P   R

3943 GAA ATC TTC GAA TTG AAG CAT TTA TCG AGG ATC AAC ACA AGT GCG AAC AAC ATC
     --- --- --- --- --- --- --- --- --- --- --- --- --- --- --- --- --- ---
      E   I   F   E   L   K   H   L   S   R   I   N   T   S   A   N   N   I

3997 ACC GGC GGT ATT CCA GAT TCA ATC TCT CGC TGC TCA ACT TTA ATC TCC GTC GAT
     --- --- --- --- --- --- --- --- --- --- --- --- --- --- --- --- --- ---
      T   G   G   I   P   D   S   I   S   R   C   S   T   L   I   S   V   D

4051 CTC AGC CGT AAC CGA ATC AAC GGA GAA ATC CCT AAA GGG ATC AAC AAC GTG AAA
     --- --- --- --- --- --- --- --- --- --- --- --- --- --- --- --- --- ---
      L   S   R   N   R   I   N   G   E   I   P   K   G   I   N   N   V   K

4105 AAC TTA GGA ACT CTA AAT ATC TCC GGT AAT CAA TTA ACC GGT TCA ATC CCT ACC
     --- --- --- --- --- --- --- --- --- --- --- --- --- --- --- --- --- ---
      N   L   G   T   L   N   I   S   G   N   Q   L   T   G   S   I   P   T

4159 GGA ATC GGA AAC ATG ACG AGT TTA ACA ACT CTC GAT CTC TCT TTC AAC GAT CTC
     --- --- --- --- --- --- --- --- --- --- --- --- --- --- --- --- --- ---
      G   I   G   N   M   T   S   L   T   T   L   D   L   S   F   N   D   L
```

FIG._5E

```
4213 TCC GGT AGA GTA CCA CTC GGT GGT CAA TTC TTG GTG TTC AAC GAA ACT TCC TTC
     --- --- --- --- --- --- --- --- --- --- --- --- --- --- --- --- --- ---
      S   G   R   V   P   L   G   G   Q   F   L   V   F   N   E   T   S   F

4267 GCC GGA AAC ACT TAC CTC TGT CTC CCT CAC CGT GTC TCT TGT CCA ACA CGG CCA
     --- --- --- --- --- --- --- --- --- --- --- --- --- --- --- --- --- ---
      A   G   N   T   Y   L   C   L   P   H   R   V   S   C   P   T   R   P

4321 GGA CAA ACC TCC GAT CAC AAT CAC ACG GCG TTG TTC TCA CCG TCA AGG ATC GTA
     --- --- --- --- --- --- --- --- --- --- --- --- --- --- --- --- --- ---
      G   Q   T   S   D   H   N   H   T   A   L   F   S   P   S   R   I   V

4375 ATC ACG GTT ATC GCA GCG ATC ACC GGT TTG ATC CTA ATC AGT GTA GCG ATT CGT
     --- --- --- --- --- --- --- --- --- --- --- --- --- --- --- --- --- ---
      I   T   V   I   A   A   I   T   G   L   I   L   I   S   V   A   I   R

4429 CAG ATG AAT AAG AAG AAG AAC CAG AAA TCT CTC GCC TGG AAA CTA ACC GCC TTC
     --- --- --- --- --- --- --- --- --- --- --- --- --- --- --- --- --- ---
      Q   M   N   K   K   K   N   Q   K   S   L   A   W   K   L   T   A   F

4483 CAG AAA CTA GAT TTC AAA TCT GAA GAC GTT CTC GAG TGT CTT AAA GAA GAG AAC
     --- --- --- --- --- --- --- --- --- --- --- --- --- --- --- --- --- ---
      Q   K   L   D   F   K   S   E   D   V   L   E   C   L   K   E   E   N

4537 ATA ATC GGT AAA GGC GGC AGT GGA ATT GTC TAC CGT GGA TCA ATG CCA AAC AAC
     --- --- --- --- --- --- --- --- --- --- --- --- --- --- --- --- --- ---
      I   I   G   K   G   G   S   G   I   V   Y   R   G   S   M   P   N   N

4591 GTA GAC GTC GCG ATT AAA CGA CTC GTT GGC CGT GGG ACC GGG AGG AGC GAT CAT
     --- --- --- --- --- --- --- --- --- --- --- --- --- --- --- --- --- ---
      V   D   V   A   I   K   R   L   V   G   R   G   T   G   R   S   D   H

4645 GGA TTC ACG GCG GAG ATT CAA ACT TTG GGG AGA ATC CGC CAC CGT CAC ATA GTG
     --- --- --- --- --- --- --- --- --- --- --- --- --- --- --- --- --- ---
      G   F   T   A   E   I   Q   T   L   G   R   I   R   H   R   H   I   V
```

FIG._5F

```
4699 AGA CTT CTT GGT TAC GTA GCG AAC AAG GAT ACG AAT CTC CTT CTT TAT GAG TAC
     --- --- --- --- --- --- --- --- --- --- --- --- --- --- --- --- --- ---
      R   L   L   G   Y   V   A   N   K   D   T   N   L   L   L   Y   E   Y

4753 ATG CCT AAT GGA AGC CTT GGA GAG CTT TTG CAT GGA TCT AAA GGT GGT CAT CTT
     --- --- --- --- --- --- --- --- --- --- --- --- --- --- --- --- --- ---
      M   P   N   G   S   L   G   E   L   L   H   G   S   K   G   G   H   L

4807 CAA TGG GAG ACG AGA CAT AGA GTA GCC GTG GAA GCT GCA AAG GGC TTG TGT TAT
     --- --- --- --- --- --- --- --- --- --- --- --- --- --- --- --- --- ---
      Q   W   E   T   R   H   R   V   A   V   E   A   A   K   G   L   C   Y

4861 CTT CAC CAT GAT TGT TCA CCA TTG ATC TTG CAT AGA GAT GTT AAG TCC AAT AAC
     --- --- --- --- --- --- --- --- --- --- --- --- --- --- --- --- --- ---
      L   H   H   D   C   S   P   L   I   L   H   R   D   V   K   S   N   N

4915 ATT CTT TTG GAC TCT GAT TTT GAA GCC CAT GTT GCT GAT TTT GGG CTT GCT AAG
     --- --- --- --- --- --- --- --- --- --- --- --- --- --- --- --- --- ---
      I   L   L   D   S   D   F   E   A   H   V   A   D   F   G   L   A   K

4969 TTC TTA GTT GAT GGT GCT GCT TCT GAG TGT ATG TCT TCA ATT GCT GAC TCT TAT
     --- --- --- --- --- --- --- --- --- --- --- --- --- --- --- --- --- ---
      F   L   V   D   G   A   A   S   E   C   M   S   S   I   A   D   S   Y

5023 GGA TAC ATC GCC CCA GGT TAG TTA CAT GTC AAC AAC ATT AGT ACT CAC CAA AAT
     --- --- --- --- ---
      G   Y   I   A   P

5077 GAT ATA TGT TCT GAT TAT CAT TTT GTT TTT GGT TTG CATAGAG TAT GCA TAT ACC
                                                         --- --- --- --- ---
                                                          E   Y   A   Y   T

5132 TTG AAA GTG GAC GAG AAG AGT GAT GTG TAT AGT TTC GGA GTG GTT TTG TTG GAG
     --- --- --- --- --- --- --- --- --- --- --- --- --- --- --- --- --- ---
      L   K   V   D   E   K   S   D   V   Y   S   F   G   V   V   L   L   E
```

FIG._5G

```
5186 TTA ATA GCT GGG AAG AAA CCT GTT GGT GAA TTT GGA GAA GGA GTG GAT ATA GTT
     --- --- --- --- --- --- --- --- --- --- --- --- --- --- --- --- --- ---
      L   I   A   G   K   K   P   V   G   E   F   G   E   G   V   D   I   V

5240 AGG TGG GTG AGG AAC ACG GAA GAG GAG ATA ACT CAG CCA TCG GAT GCT GCT ATT
     --- --- --- --- --- --- --- --- --- --- --- --- --- --- --- --- --- ---
      R   W   V   R   N   T   E   E   E   I   T   Q   P   S   D   A   A   I

5294 GTT GTT GCG ATT GTT GAC CCG AGG TTG ACT GGT TAC CCG TTG ACA AGT GTG ATT
     --- --- --- --- --- --- --- --- --- --- --- --- --- --- --- --- --- ---
      V   V   A   I   V   D   P   R   L   T   G   Y   P   L   T   S   V   I

5348 CAT GTG TTC AAG ATC GCA ATG ATG TGT GTG GAG GAA GAA GCC GCG GCA AGG CCT
     --- --- --- --- --- --- --- --- --- --- --- --- --- --- --- --- --- ---
      H   V   F   K   I   A   M   M   C   V   E   E   E   A   A   A   R   P

5402 ACG ATG AGG GAA GTT GTG CAC ATG CTC ACT AAC CCT CCT AAA TCC GTG GCG AAC
     --- --- --- --- --- --- --- --- --- --- --- --- --- --- --- --- --- ---
      T   M   R   E   V   V   H   M   L   T   N   P   P   K   S   V   A   N

5456 TTG ATC GCG TTC TGA CCC AAG CAA GAT AAA TAT GAA AAT AAG ATG CGA AAT GT
     --- --- --- --- ---
      L   I   A   F   *

5509 GGT GAT CAT TTT TTG GGT GTT CTT ATT TAT GGT TTC TAA TAC TTT CGG GTT TGT
5563 ATA TTT GTT GTG TTT CAA TTT GTA TAT TAC CTC TTT ATG TGT TAT TAT CTC GAG
5617 TAT GTA ATG TAA TCA ATA TGC TTA TTG CTT GAT GGC TTT AAA CTT TAG CTA ATT
5671 CTC CGT TCA GAG TGT ATA AAA TAA AAG AAT GTG AGA GCT TTG ACC TCT GGA TTT
5725 AAG TCT AGA 3'
```

FIG._5H

```
          ar V is L n V sf T p LFG t I
S pe I gm L th L vn L t L aa N n FTG e L
P le M ks L ts L kv L n I sn N n LTG t F
Pgei L ka M vd L ev L d T yngN n FNG k L
P pe M se L kk L ky L s F gg N f FSG e I
P es Y gd I qs L ey L g L ng A g LSG k S
P af L sr L kn L re M y I gyyN s YTG g V
P re F gg L tk L ei L d M as C t LTG e I
P ts L sn L kh L ht L f L hi N n LTG h I
P pe L sg L vs L ks L d L si N q LTG e I
P qs F in L gn I tl I n L fr N n LYG q I
P ea I ge L pk L ev F e V we N n FTL q L
P an L gr N gn L ik L d V sd N h LTG l I
P kd L cr G ek L em L i L sn N f FFG p I
P ee L gk C ks L tk I r I vk N l LNG t V
P ag L fn L pl V ti I e L td N f FSG e L
P  v T ms G dv L dq I y L sn N w FSG e I
P pa I gn F pn L qt L f L dr N r FRG n I
P re I fe L kh L sr I n T sa N n ITG g I
P ds I sr C st L is V d L sr N r ING e I
P kg I nn V kn L gt L n I sg N q LTG s I
P tg I gn M ts L tt L d L sf N d LSG r V

P xx L xx L xx L xx L x L xx N x LTG x I
```

*FIG._6A*

```
GkGgSGiVyrgsmpnnvdvAiKrlvgrgtgrsdhgftaEiqtlgrirhrhivrllgyv
    F

ankdtnlllyeympnGsLgellhgskgghlqwetrhrvaveaakGLcylhhdcsplil
                                             M

HRDVKsnNilldsdfeaHvaDFGlaKflvdgaasecmssiagSygYiaPEyaytlkvd
   L              K       R                P  W

ekSDVYsfGvvllEliagkkPVgefgegvdivrwvrnteeeitqpsdaaivvaivDpr
     W               Y                                   G

ltgyPltsvihvfkiammCveeeaaaRPtmrevvhmltnppksvanliaF
                   W         F
```

*FIG._6B*

```
CLV1   MAMRLLKTHLLFLHLYLFFSPCFAYTDMEVLLNLKSSMIGPKGHGLHDWI
RLK5   M----LYCLILLLCLSSTYLPSLSLNQDATILRQAKLGLSDPAQSLSSWS
       *    *   .*.* *   . * ..  .   .*       ..  ...*  *

CLV1   HSSSPDAHCSFSGVSCDDDARVISLNVSFTPLFGTISPEIGMLTHLVNLT
RLK5   DNNDVTP-CKWLGVSCDATSNVVSVDLSSFMLVGPFPSILCHLPSLHSLS
       ...    . *   *****  . *.*...*   * * ... .   *  * .*.

CLV1   LAANNFTGELPLE-MKSLTSLKVLNISNNGNLTGTFPGEILKAMVDLEVL
RLK5   LYNNSINGSLSADDFDTCHNLISLDLSEN-LLVGSIPKSLPFNLPNLKFL
       *  *.. * *. .   .  .*  *..*.*  * *..*   .    . .*  *

CLV1   DTYNNNFNGKLPPEMSELKKLKYLSFGGNFFSGEIPESYGDIQSLEYLGL
RLK5   EISGNNLSDTIPSSFGEFRKLESLNLAGNFLSGTIPASLGNVTTLKELKL
       .    **... .*.  .*..**  *...***.** ** * *.. .*  * *

CLV1   NGAGLS-GKSPAFLSRLKNLREMYIGYYNSYTGGVPREFGGLTKLEILDM
RLK5   AYNLFSPSQIPSQLGNLTELQVLWLAGCN-LVGPIPPSLSRLTSLVNLDL
           .* .. *. *. * .*. . ..  *   * .*  .. ** *  **.

CLV1   ASCTLTGEIPTSLSNLKHLHTLFLHINNLTGHIPPELSGLVSLKSLDLSI
RLK5   TFNQLTGSIPSWITQLKTVEQIELFNNSFSGELPESMGNMTTLKRFDASM
       .   *** **. ...**  .. .  *  *...*..*  .. . .** .* *.

CLV1   NQLTGEIPQSFINLGNITLINLFRNNLYGQIPEAIGELPKLEVFEVWENN
RLK5   NKLTGKIPDNL-NLLNLESLNLFENMLEGPLPESITRSKTLSELKLFNNR
       *.*** **... ** *.  .*** * * * .**.*      *   . . .*

CLV1   FTLQLPANLGRNGNLIKLDVSDNHLTGLIPKDLCRGEKLEMLILSNNFFF
RLK5   LTGVLPSQLGANSPLQYVDLSYNRFSGEIPANVCGEGKLEYLILIDNSFS
       .*  **..** *. *  .*.* *...* ** ..*    *** *** .* *

CLV1   GPIPEELGKCKSLTKIRIVKNLLNGTVPAGLFNLPLVTIIELTDNFFSGE
RLK5   GEISNNLGKCKSLTRVRLSNNKLSGQIPHGFWGLPRLSLLELSDNSFTGS
       * *...********..*. .* *.* .* *.  **  ....**.** *.*

CLV1   LPVTMSGDV-LDQIYLSNNWFSGEIPPAIGNFPNLQTLFLDRNRFRGNIP
RLK5   IPKTIIGAKNLSNLRISKNRFSGSIPNEIGSLNGIIEISGAENDFSGEIP
       .* *. *    * .. .*.*.*** **  **..  .  .      * * *.**

CLV1   REIFELKHLSRINTSANNITGGIPDSISRCSTLISVDLSRNRINGEIPKG
RLK5   ESLVKLKQLSRLDLSKNQLSGEIPRELRGWKNLNELNLANNHLSGEIPKE
        .  **.***.. * *...* **  .      *  ..*. *...*****

CLV1   INNVKNLGTLNISGNQLTGSIPTGIGNMTSLTTLDLSFNDLSGRVPLGGQ
RLK5   VGILPVLNYLDLSSNQFSGEIPLELQNLK-LNVLNLSYNHLSGKIPPLYA
       .  .  *  *..*.**..* **  .*.  *  *.**.*.***..*

CLV1   FLVFNETSFAGNTYLCLPHRVSCPTRPGQTSDHNHTALFSPSRIVITVIA
RLK5   NKIYAHD-FIGNPGLCVDLDGLC--RKITRSKNIGYVWILLTIFLLAGLV
        .. .   * **  **.      *  *    * .     .  . .... .

CLV1   AITGLILISVAIRQMNKKKNQKSLAWKLTAFQKLDFKSEDVLECLKEENI
RLK5   FVVGIVMFIAKCRKLRALKSSTLAASKWRSFHKLHFSEHEIADCLDEKNV
        . *....     *..   *.     * *  .*.**.*   ... .** * *.
```

*FIG._8A*

```
CLV1    IGKGGSGIVYRGSMPNNVDVAIKRLVGRGTGRSDH---------GFTAEI
RLK5    IGFGSSGKVYKVELRGGEVVAVKKLNKSVKGGDDEYSSDSLNRDVFAAEV
        ** *.** **.  .     **.*.*     *  *.          *.**.

CLV1    QTLGRIRHRHIVRLLGYVANKDTNLLLYEYMPNGSLGELLHGSK--GGHL
RLK5    ETLGTIRHKSIVRLWCCCSSGDCKLLVYEYMPNGSLADVLHGDRKGGVVL
        .*** ***. ****    .. * .**.*********...*** .  *  *

CLV1    QWETRHRVAVEAAKGLCYLHHDCSPLILHRDVKSNNILLDSDFEAHVADF
RLK5    GWPERLRIALDAAEGLSYLHHDCVPPIVHRDVKSSNILLDSDYGAKVADF
         *  * *.*..** ** ****** * *.******.*******. * ****

CLV1    GLAKF--LVDGAASECMSSIAGSYGYIAPEYAYTLKVDEKSDVYSFGVVL
RLK5    GIAKVGQMSGSKTPEAMSGIAGSCGYIAPEYVYTLRVNEKSDIYSFGVVL
        *.**   . .. ..* **.**.* ******* ***.*.****.*******

CLV1    LELIAGKKPVGEFGEGVDIVRWVRNTEEEITQPSDAAIVVAIVDPRLTGY
RLK5    LELVTGKQPTDSELGDKDMAKWVCTALDKCG-------LEPVIDPKLDLK
        ***..**.* .    . *. .**   . .          . ...**.*

CLV1    PLTSVIHVFKIAMMCVEEEAAARPTMREVVHML--------------TNP
RLK5    FKEEISKVIHIGLLCTSPLPLNRPSMRKVVIMLQEVSGAVPCSSPNTSKR
            .  *. *...*    .  **.** ** **              ..

CLV1    PKSVANLIAF--------
RLK5    SKTGGKLSPYYTEDLNSV
        .*. ..* ..
```

CGCTCTTTCTCACTGAGAGGACACTAAAAAAATGGCGATGAGACTTTTGAAGAC
TCATCTTCTGTTTCTGCATCTGTATCTATTTTTCTCACCATGTTTCGCTTACAC
TGACATGGAAGTTCTTCTCAATCTCAAATCCTCCATGATTGGTCCTAAAGGACA
CGGTCTCCACGACTGGATTCACTCATCTTCTCCGGATGCTCACTGTTCTTTCTC
CGGCGTCTCATGTGACGACGATGCTCGTGTTATCTCTCTCAACGTCTCCTTCAC
TCCTTTGTTTGGTACAATCTCACCAGAGATTGGGATGTTGACTCATTTGGTGAA
TCTAACTTTAGC

CGGAGTGGTTTTGTTGGAGTTAATAGCTGGGAAGAAACCTGTTGGTGAATTTGG
AGAAGGAGTGGATATAGTTAGGTGGGTGAGGAACACGGAAGAGGAGATAACTCA
GCCATCGGATGCTGCTATTGTTGTTGCGATTGTTGACCCGAGGTTGACTGGTTA
CCCGTTGACAAGTGTGATTCATGTGTTCAAGATCGCAATGATGTGTGTGGAGGA
AGAAGCCGCGGCAAGGCCTACGATGAGGGAAGTTGTGCACATGCTCACTAACCC
TCCTAAATCCGTGGCGAACTTGATCGCGTTCTGACCCAAGCAAGATAA

FIG._ 9B

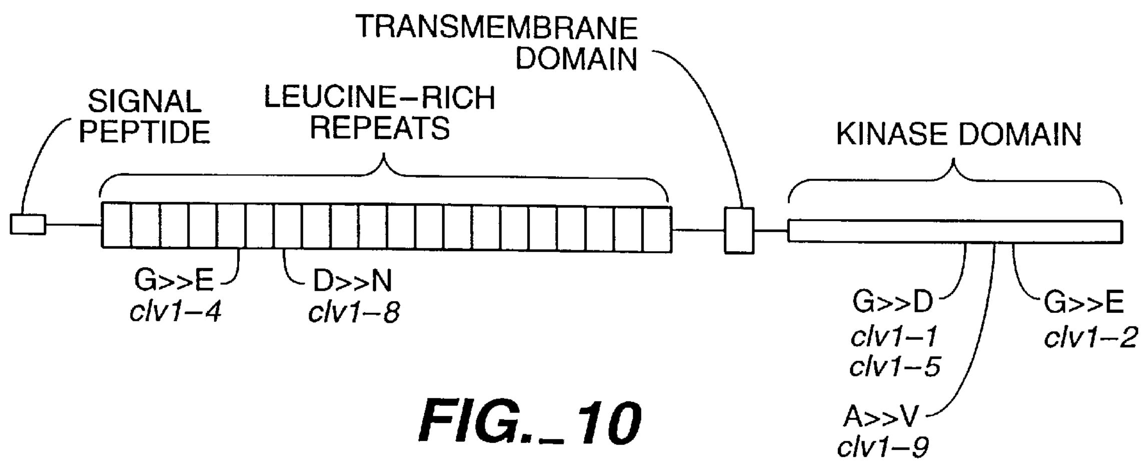

FIG._10

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 5733 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
( A ) NAME/KEY: CDS
( B ) LOCATION: 2434..5037

( i x ) FEATURE:
( A ) NAME/KEY: CDS
( B ) LOCATION: 5117..5467

-continued ( x i ) SEQUENCE DESCRIPTION: SEQ ID NO:1:

```
TCTAGAAATT GGTCCAAAGT TCTTTCACCC GTGAGTCATT TAGTGATAAA GATGACATGA    60
TTTTTGGTGA TAAATTTTCC ATCGTTGCTA TATGTCGTTA TATTATTCTC CTATATGTAT   120
ATTATACTAT TTACATCAGA AAATAATCCA AAGTTTAGAG ATTCTTTTTT ACAATAATAA   180
AATTTCCCAC TTACTAAAAA GAGCTCCTTT TCTGCTGAAG AGAACCTAAA CCTTTATTCC   240
CAAAGTTCAT TGAGTTAGAG CATTTTCAGC GAATCACATA AGAGATGCTC TCTTCTTCAT   300
CACTAATTGA CATCTCATTG TTTTAAAGGT TGCACTTGTA CCTGTTGATC TGATTCTCAA   360
TCCACTTAAG TTAAACCAAA TAGACACGAG AAAAAAGCAC ATTTATTTGT TGCTAAGTAT   420
GCATATTTTT CAGCGTTTAC TTCTTAATCT AATGTATATC ATAAGATAAT ATCTAAAAGA   480
GAATGCACAA AAGATTATTA ATATGAGAAA TTCGCTGCCA TTTAGGAAGG ACCTTTATAC   540
CAATATACCG CAATAATAAT AGAACATTGG TCCCCAAGTG TATGTCAACC CCAAGTGTAT   600
AGATTTCTTT AAAGATTAAA ATCCCTTTTT GTTGCTAAAG CACCTGATAT ATTTTTCTAT   660
CAAACTAAAA AAATTGTTAG CGGGATGAAG ATATATTCGC CAAGAACCAT AGTGCTTGTA   720
TAACGGCAGA CCATTAATTC ACAACTATTA TTATTTTATT GTTAGATTGT TGATAGAATC   780
GATTTTGATT GTGGCAGAAT CGATCTTGTA AAAACTGCTT AAGGTGCTTA CTTATAATTA   840
AGAAAGATTC ACTTATGTAA GTTAAGCATA TTAATCATAT CATTCGGCCT AATTCATTAG   900
GAATATTTTG CTATTCGTTT TGCCATCATT AACAACAAAA TTGACACGTT TTCAGCCAAA   960
AGTATTAACA ACTAAACCTA AAACTTCAAA CATTAAATAG TTTTTAGTAT CTTTAGTTTC  1020
AAACTAGTGA TTTGTCCTAA TATCAACACT ACGAACGAAT TTATATACAT TGAACTTTTT  1080
TCTGAATCAC CGATTACAAA ACGAATATAA TTTGGTATCG GCAGTTGCTA TTAATTTGAT  1140
CGGTTTGGAC TTTGGACTAA TCACGATCAA ATCTTAAATG GACCGAAGTG AATAAATCCC  1200
TAATGTTTTC AAGAGAGTCA CACGAACGAA ACAAAGGTAA AATATGAACA TAGAGCGTGG  1260
GGACTTGAAG CAGAAGGTCT GTATGGTGAC ATACCGGTGA GTGGAGTGTA TGAATGAACG  1320
AGAAGTGAGA AGACAAAATA CAAGAAAGAG CGTTGACTTG GAAGTTAAAG CCAAAAAAAC  1380
CACAAGGGGC AAATTTGTCT CTTTAGGAAA AGGACACAGA CAGACTTTCT ATACGGGCCA  1440
ATTAGAAAAA TAGGCCCTAC TTCTAATTAA AGCCCATTTA CTTCTCTCCT TGTCTTCTTA  1500
TTCCTCTTTT CTCCCCATCA CGTGACGACG ATGCTATAAA CGCCGTCGAT TATATAACTG  1560
GTGCCGTTGA CAGACGGCGA CAGAAGAAAG AAAGAAGAAA CCACAGGCTC TAGGGAACGT  1620
AACGTTATGT CCTGTCTATA GCATTTATAA CGGTCAGATC AACGCCGTTT AGATAAAGAT  1680
CTGTCAATGT TAAAGAAGAG ATGCATCTCT ACACCGTTAA ATTTAAAACG CCGTGAACCT  1740
CTTATCTATT GATTTTTGTT TGATGAAGCC AAAACAAATC GTGTCAGAAG ACTTATCAGA  1800
GAAGAAGAAA ACGACGACGT TCCCGTTTCT CCATGTCTAA TAAGTGTAGT AGTGGCGGCT  1860
ACTAAAAACT CTAAAGTTTG ACTCCAGTAA AACTGCCTTT CTAGTGTAAT TCCAGTGATT  1920
TTAGAGTTTG AATAGTGTGT GACCAAATTT GAAAGTACAA TCTCAGCAAT ATTATTGATC  1980
ACTCGTTATA AAAGAATCGA ATGTAAAAAT AGCCAATGAG AGACTGAGAC GTATGTGTTT  2040
GACCATAAGT CGTATAGTTT GTATCTATCT ACCTGCAAGA TCAGCAGATG GTTCTCTGAT  2100
CAATTGTACC TTAATTATCT TTTATTTTCG TAAAATTTCT CTATTCACAA ATGATAAATC  2160
TACTTAAGAC AGTAACCATA ACAAGATTTA CAAGATAATT TGAAAAATGA ACACATAAAA  2220
GTATTTTGGC GCATTATTTT TAATAATAAC AATATTTATG TAAAGTCACA TAAAAGTATA  2280
TATTCGCTCA CAAAGTCTTA CGGTATTTAG AACAGTAGTA CCACATCGAT TCTCTTCATC  2340
```

```
TTCTTCTTCA TAATATGCCA TTGTTCATGT CTCTGTGTCC TATCGCATAA CACTCACGCT   2400

ATCTTATTAT TTTCTCTCGC TCTTTCTCAC TGA GAG GAC ACT AAA AAA ATG GCG    2454
                                     Glu Asp Thr Lys Lys Met Ala
                                     1               5

ATG AGA CTT TTG AAG ACT CAT CTT CTG TTT CTG CAT CTG TAT CTA TTT    2502
Met Arg Leu Leu Lys Thr His Leu Leu Phe Leu His Leu Tyr Leu Phe
        10                  15                  20

TTC TCA CCA TGT TTC GCT TAC ACT GAC ATG GAA GTT CTT CTC AAT CTC    2550
Phe Ser Pro Cys Phe Ala Tyr Thr Asp Met Glu Val Leu Leu Asn Leu
    25                  30                  35

AAA TCC TCC ATG ATT GGT CCT AAA GGA CAC GGT CTC CAC GAC TGG ATT    2598
Lys Ser Ser Met Ile Gly Pro Lys Gly His Gly Leu His Asp Trp Ile
40                  45                  50                  55

CAC TCA TCT TCT CCG GAT GCT CAC TGT TCT TTC TCC GGC GTC TCA TGT    2646
His Ser Ser Ser Pro Asp Ala His Cys Ser Phe Ser Gly Val Ser Cys
                60                  65                  70

GAC GAC GAT GCT CGT GTT ATC TCT CTC AAC GTC TCC TTC ACT CCT TTG    2694
Asp Asp Asp Ala Arg Val Ile Ser Leu Asn Val Ser Phe Thr Pro Leu
            75                  80                  85

TTT GGT ACA ATC TCA CCA GAG ATT GGG ATG TTG ACT CAT TTG GTG AAT    2742
Phe Gly Thr Ile Ser Pro Glu Ile Gly Met Leu Thr His Leu Val Asn
        90                  95                  100

CTA ACT TTA GCT GCC AAC AAC TTC ACC GGT GAA TTA CCA TTG GAG ATG    2790
Leu Thr Leu Ala Ala Asn Asn Phe Thr Gly Glu Leu Pro Leu Glu Met
    105                 110                 115

AAG AGT CTA ACT TCT CTC AAG GTT TTG AAT ATC TCC AAC AAT GGT AAC    2838
Lys Ser Leu Thr Ser Leu Lys Val Leu Asn Ile Ser Asn Asn Gly Asn
120                 125                 130                 135

CTT ACT GGA ACA TTC CCT GGA GAG ATT TTA AAA GCT ATG GTT GAT CTT    2886
Leu Thr Gly Thr Phe Pro Gly Glu Ile Leu Lys Ala Met Val Asp Leu
                140                 145                 150

GAA GTT CTT GAC ACT TAT AAC AAC AAT TTC AAC GGT AAG TTA CCA CCG    2934
Glu Val Leu Asp Thr Tyr Asn Asn Asn Phe Asn Gly Lys Leu Pro Pro
            155                 160                 165

GAG ATG TCA GAG CTT AAG AAG CTT AAA TAC CTC TCT TTC GGT GGA AAT    2982
Glu Met Ser Glu Leu Lys Lys Leu Lys Tyr Leu Ser Phe Gly Gly Asn
        170                 175                 180

TTC TTC AGC GGA GAG ATT CCA GAG AGT TAT GGA GAT ATT CAA AGC TTA    3030
Phe Phe Ser Gly Glu Ile Pro Glu Ser Tyr Gly Asp Ile Gln Ser Leu
    185                 190                 195

GAG TAT CTT GGT CTC AAC GGA GCT GGA CTC TCC GGT AAA TCT CCG GCG    3078
Glu Tyr Leu Gly Leu Asn Gly Ala Gly Leu Ser Gly Lys Ser Pro Ala
200                 205                 210                 215

TTT CTT TCC CGC CTC AAG AAC TTA AGA GAA ATG TAT ATT GGC TAC TAC    3126
Phe Leu Ser Arg Leu Lys Asn Leu Arg Glu Met Tyr Ile Gly Tyr Tyr
                220                 225                 230

AAC AGC TAC ACC GGT GGT GTT CCA CGC GAG TTC GGT GGT TTA ACA AAG    3174
Asn Ser Tyr Thr Gly Gly Val Pro Arg Glu Phe Gly Gly Leu Thr Lys
            235                 240                 245

CTT GAG ATC CTC GAC ATG GCG AGC TGT ACA CTC ACC GGA GAG ATT CCG    3222
Leu Glu Ile Leu Asp Met Ala Ser Cys Thr Leu Thr Gly Glu Ile Pro
        250                 255                 260

ACG AGT TTA AGT AAC CTG AAA CAT CTA CAT ACT CTG TTT CTT CAC ATC    3270
Thr Ser Leu Ser Asn Leu Lys His Leu His Thr Leu Phe Leu His Ile
    265                 270                 275

AAC AAC TTA ACC GGT CAT ATA CCA CCG GAG CTT TCC GGT TTA GTC AGC    3318
Asn Asn Leu Thr Gly His Ile Pro Pro Glu Leu Ser Gly Leu Val Ser
280                 285                 290                 295

TTG AAA TCT CTC GAT TTA TCA ATC AAT CAG TTA ACC GGA GAA ATC CCT    3366
```

-continued

```
Leu   Lys   Ser   Leu   Asp   Leu   Ser   Ile   Asn   Gln   Leu   Thr   Gly   Glu   Ile   Pro
                        300                           305                           310

CAA   AGC   TTC   ATC   AAT   CTC   GGA   AAC   ATT   ACT   CTA   ATC   AAT   CTC   TTC   AGA        3414
Gln   Ser   Phe   Ile   Asn   Leu   Gly   Asn   Ile   Thr   Leu   Ile   Asn   Leu   Phe   Arg
                  315                           320                           325

AAC   AAT   CTC   TAC   GGA   CAA   ATA   CCA   GAG   GCC   ATC   GGA   GAA   TTA   CCA   AAA        3462
Asn   Asn   Leu   Tyr   Gly   Gln   Ile   Pro   Glu   Ala   Ile   Gly   Glu   Leu   Pro   Lys
            330                           335                           340

CTC   GAA   GTC   TTC   GAA   GTA   TGG   GAG   AAC   AAT   TTC   ACG   TTA   CAA   TTA   CCG        3510
Leu   Glu   Val   Phe   Glu   Val   Trp   Glu   Asn   Asn   Phe   Thr   Leu   Gln   Leu   Pro
      345                           350                           355

GCG   AAT   CTT   GGC   CGG   AAC   GGG   AAT   CTA   ATA   AAG   CTT   GAT   GTC   TCT   GAT        3558
Ala   Asn   Leu   Gly   Arg   Asn   Gly   Asn   Leu   Ile   Lys   Leu   Asp   Val   Ser   Asp
360                           365                           370                           375

AAT   CAT   CTC   ACC   GGA   CTT   ATC   CCC   AAG   GAC   TTA   TGC   AGA   GGT   GAG   AAA        3606
Asn   His   Leu   Thr   Gly   Leu   Ile   Pro   Lys   Asp   Leu   Cys   Arg   Gly   Glu   Lys
                        380                           385                           390

TTA   GAG   ATG   TTA   ATT   CTC   TCT   AAC   AAC   TTC   TTC   TTT   GGT   CCA   ATT   CCA        3654
Leu   Glu   Met   Leu   Ile   Leu   Ser   Asn   Asn   Phe   Phe   Phe   Gly   Pro   Ile   Pro
                  395                           400                           405

GAA   GAG   CTT   GGT   AAA   TGC   AAA   TCC   TTA   ACC   AAA   ATC   AGA   ATC   GTT   AAG        3702
Glu   Glu   Leu   Gly   Lys   Cys   Lys   Ser   Leu   Thr   Lys   Ile   Arg   Ile   Val   Lys
            410                           415                           420

AAT   CTT   CTC   AAC   GGC   ACT   GTT   CCG   GCG   GGG   CTT   TTC   AAT   CTA   CCG   TTA        3750
Asn   Leu   Leu   Asn   Gly   Thr   Val   Pro   Ala   Gly   Leu   Phe   Asn   Leu   Pro   Leu
      425                           430                           435

GTT   ACG   ATT   ATC   GAA   CTC   ACT   GAT   AAT   TTC   TTC   TCC   GGT   GAA   CTT   CCG        3798
Val   Thr   Ile   Ile   Glu   Leu   Thr   Asp   Asn   Phe   Phe   Ser   Gly   Glu   Leu   Pro
440                           445                           450                           455

GTA   ACG   ATG   TCC   GGC   GAT   GTT   CTC   GAT   CAG   ATT   TAC   CTC   TCT   AAC   AAC        3846
Val   Thr   Met   Ser   Gly   Asp   Val   Leu   Asp   Gln   Ile   Tyr   Leu   Ser   Asn   Asn
                        460                           465                           470

TGG   TTT   TCC   GGC   GAG   ATT   CCA   CCT   GCG   ATT   GGT   AAT   TTC   CCC   AAT   CTA        3894
Trp   Phe   Ser   Gly   Glu   Ile   Pro   Pro   Ala   Ile   Gly   Asn   Phe   Pro   Asn   Leu
                  475                           480                           485

CAG   ACT   CTA   TTC   TTA   GAT   CGG   AAC   CGA   TTT   CGC   GGC   AAC   ATT   CCG   AGA        3942
Gln   Thr   Leu   Phe   Leu   Asp   Arg   Asn   Arg   Phe   Arg   Gly   Asn   Ile   Pro   Arg
            490                           495                           500

GAA   ATC   TTC   GAA   TTG   AAG   CAT   TTA   TCG   AGG   ATC   AAC   ACA   AGT   GCG   AAC        3990
Glu   Ile   Phe   Glu   Leu   Lys   His   Leu   Ser   Arg   Ile   Asn   Thr   Ser   Ala   Asn
      505                           510                           515

AAC   ATC   ACC   GGC   GGT   ATT   CCA   GAT   TCA   ATC   TCT   CGC   TGC   TCA   ACT   TTA        4038
Asn   Ile   Thr   Gly   Gly   Ile   Pro   Asp   Ser   Ile   Ser   Arg   Cys   Ser   Thr   Leu
520                           525                           530                           535

ATC   TCC   GTC   GAT   CTC   AGC   CGT   AAC   CGA   ATC   AAC   GGA   GAA   ATC   CCT   AAA        4086
Ile   Ser   Val   Asp   Leu   Ser   Arg   Asn   Arg   Ile   Asn   Gly   Glu   Ile   Pro   Lys
                        540                           545                           550

GGG   ATC   AAC   AAC   GTG   AAA   AAC   TTA   GGA   ACT   CTA   AAT   ATC   TCC   GGT   AAT        4134
Gly   Ile   Asn   Asn   Val   Lys   Asn   Leu   Gly   Thr   Leu   Asn   Ile   Ser   Gly   Asn
                  555                           560                           565

CAA   TTA   ACC   GGT   TCA   ATC   CCT   ACC   GGA   ATC   GGA   AAC   ATG   ACG   AGT   TTA        4182
Gln   Leu   Thr   Gly   Ser   Ile   Pro   Thr   Gly   Ile   Gly   Asn   Met   Thr   Ser   Leu
            570                           575                           580

ACA   ACT   CTC   GAT   CTC   TCT   TTC   AAC   GAT   CTC   TCC   GGT   AGA   GTA   CCA   CTC        4230
Thr   Thr   Leu   Asp   Leu   Ser   Phe   Asn   Asp   Leu   Ser   Gly   Arg   Val   Pro   Leu
      585                           590                           595

GGT   GGT   CAA   TTC   TTG   GTG   TTC   AAC   GAA   ACT   TCC   TTC   GCC   GGA   AAC   ACT        4278
Gly   Gly   Gln   Phe   Leu   Val   Phe   Asn   Glu   Thr   Ser   Phe   Ala   Gly   Asn   Thr
600                           605                           610                           615

TAC   CTC   TGT   CTC   CCT   CAC   CGT   GTC   TCT   TGT   CCA   ACA   CGG   CCA   GGA   CAA        4326
```

-continued

```
Tyr Leu Cys Leu Pro His Arg Val Ser Cys Pro Thr Arg Pro Gly Gln
                620                 625                 630

ACC TCC GAT CAC AAT CAC ACG GCG TTG TTC TCA CCG TCA AGG ATC GTA      4374
Thr Ser Asp His Asn His Thr Ala Leu Phe Ser Pro Ser Arg Ile Val
            635                 640                 645

ATC ACG GTT ATC GCA GCG ATC ACC GGT TTG ATC CTA ATC AGT GTA GCG      4422
Ile Thr Val Ile Ala Ala Ile Thr Gly Leu Ile Leu Ile Ser Val Ala
        650                 655                 660

ATT CGT CAG ATG AAT AAG AAG AAG AAC CAG AAA TCT CTC GCC TGG AAA      4470
Ile Arg Gln Met Asn Lys Lys Lys Asn Gln Lys Ser Leu Ala Trp Lys
    665                 670                 675

CTA ACC GCC TTC CAG AAA CTA GAT TTC AAA TCT GAA GAC GTT CTC GAG      4518
Leu Thr Ala Phe Gln Lys Leu Asp Phe Lys Ser Glu Asp Val Leu Glu
680                 685                 690                 695

TGT CTT AAA GAA GAG AAC ATA ATC GGT AAA GGC GGC AGT GGA ATT GTC      4566
Cys Leu Lys Glu Glu Asn Ile Ile Gly Lys Gly Gly Ser Gly Ile Val
                700                 705                 710

TAC CGT GGA TCA ATG CCA AAC AAC GTA GAC GTC GCG ATT AAA CGA CTC      4614
Tyr Arg Gly Ser Met Pro Asn Asn Val Asp Val Ala Ile Lys Arg Leu
            715                 720                 725

GTT GGC CGT GGG ACC GGG AGG AGC GAT CAT GGA TTC ACG GCG GAG ATT      4662
Val Gly Arg Gly Thr Gly Arg Ser Asp His Gly Phe Thr Ala Glu Ile
        730                 735                 740

CAA ACT TTG GGG AGA ATC CGC CAC CGT CAC ATA GTG AGA CTT CTT GGT      4710
Gln Thr Leu Gly Arg Ile Arg His Arg His Ile Val Arg Leu Leu Gly
    745                 750                 755

TAC GTA GCG AAC AAG GAT ACG AAT CTC CTT CTT TAT GAG TAC ATG CCT      4758
Tyr Val Ala Asn Lys Asp Thr Asn Leu Leu Leu Tyr Glu Tyr Met Pro
760                 765                 770                 775

AAT GGA AGC CTT GGA GAG CTT TTG CAT GGA TCT AAA GGT GGT CAT CTT      4806
Asn Gly Ser Leu Gly Glu Leu Leu His Gly Ser Lys Gly Gly His Leu
                780                 785                 790

CAA TGG GAG ACG AGA CAT AGA GTA GCC GTG GAA GCT GCA AAG GGC TTG      4854
Gln Trp Glu Thr Arg His Arg Val Ala Val Glu Ala Ala Lys Gly Leu
            795                 800                 805

TGT TAT CTT CAC CAT GAT TGT TCA CCA TTG ATC TTG CAT AGA GAT GTT      4902
Cys Tyr Leu His His Asp Cys Ser Pro Leu Ile Leu His Arg Asp Val
        810                 815                 820

AAG TCC AAT AAC ATT CTT TTG GAC TCT GAT TTT GAA GCC CAT GTT GCT      4950
Lys Ser Asn Asn Ile Leu Leu Asp Ser Asp Phe Glu Ala His Val Ala
    825                 830                 835

GAT TTT GGG CTT GCT AAG TTC TTA GTT GAT GGT GCT GCT TCT GAG TGT      4998
Asp Phe Gly Leu Ala Lys Phe Leu Val Asp Gly Ala Ala Ser Glu Cys
840                 845                 850                 855

ATG TCT TCA ATT GCT GAC TCT TAT GGA TAC ATC GCC CCA GGTTAGTTAC       5047
Met Ser Ser Ile Ala Asp Ser Tyr Gly Tyr Ile Ala Pro
                860                 865

ATGTCAACAA CATTAGTACT CACCAAAATG ATATATGTTC TGATTATCAT TTTGTTTTTG    5107

GTTTGCATA GAG TAT GCA TAT ACC TTG AAA GTG GAC GAG AAG AGT GAT         5155
          Glu Tyr Ala Tyr Thr Leu Lys Val Asp Glu Lys Ser Asp
           1               5                  10

GTG TAT AGT TTC GGA GTG GTT TTG TTG GAG TTA ATA GCT GGG AAG AAA      5203
Val Tyr Ser Phe Gly Val Val Leu Leu Glu Leu Ile Ala Gly Lys Lys
     15                 20                  25

CCT GTT GGT GAA TTT GGA GAA GGA GTG GAT ATA GTT AGG TGG GTG AGG      5251
Pro Val Gly Glu Phe Gly Glu Gly Val Asp Ile Val Arg Trp Val Arg
 30                 35                  40                  45

AAC ACG GAA GAG GAG ATA ACT CAG CCA TCG GAT GCT GCT ATT GTT GTT      5299
Asn Thr Glu Glu Glu Ile Thr Gln Pro Ser Asp Ala Ala Ile Val Val
                50                  55                  60
```

```
GCG ATT GTT GAC CCG AGG TTG ACT GGT TAC CCG TTG ACA AGT GTG ATT     5347
Ala Ile Val Asp Pro Arg Leu Thr Gly Tyr Pro Leu Thr Ser Val Ile
             65                  70                  75

CAT GTG TTC AAG ATC GCA ATG ATG TGT GTG GAG GAA GAA GCC GCG GCA     5395
His Val Phe Lys Ile Ala Met Met Cys Val Glu Glu Glu Ala Ala Ala
         80                  85                  90

AGG CCT ACG ATG AGG GAA GTT GTG CAC ATG CTC ACT AAC CCT CCT AAA     5443
Arg Pro Thr Met Arg Glu Val Val His Met Leu Thr Asn Pro Pro Lys
     95                 100                 105

TCC GTG GCG AAC TTG ATC GCG TTC TGACCCAAGC AAGATAAATA TGAAAATAAG    5497
Ser Val Ala Asn Leu Ile Ala Phe
110                 115

ATGCGAAATG TGGTGATCAT TTTTTGGGTG TTCTTATTTA TGGTTTCTAA TACTTTCGGG   5557

TTTGTATATT TGTTGTGTTT CAATTTGTAT ATTACCTCTT TATGTGTTAT TATCTCGAGT   5617

ATGTAATGTA ATCAATATGC TTATTGCTTG ATGGCTTTAA ACTTTAGCTA ATTCTCCGTT   5677

CAGAGTGTAT AAAATAAAAG AATGTGAGAG CTTTGACCTC TGGATTTAAG TCTAGA       5733
```

(2) INFORMATION FOR SEQ ID NO:2:

(i) SEQUENCE CHARACTERISTICS:
(A) LENGTH: 985 amino acids
(B) TYPE: amino acid
(D) TOPOLOGY: linear (ii) MOLECULE TYPE: protein (xi) SEQUENCE DESCRIPTION: SEQ ID NO:2:

```
Glu Asp Thr Lys Lys Met Ala Met Arg Leu Leu Lys Thr His Leu Leu
  1               5                  10                  15

Phe Leu His Leu Tyr Leu Phe Phe Ser Pro Cys Phe Ala Tyr Thr Asp
             20                  25                  30

Met Glu Val Leu Leu Asn Leu Lys Ser Ser Met Ile Gly Pro Lys Gly
         35                  40                  45

His Gly Leu His Asp Trp Ile His Ser Ser Ser Pro Asp Ala His Cys
     50                  55                  60

Ser Phe Ser Gly Val Ser Cys Asp Asp Asp Ala Arg Val Ile Ser Leu
 65                  70                  75                  80

Asn Val Ser Phe Thr Pro Leu Phe Gly Thr Ile Ser Pro Glu Ile Gly
                 85                  90                  95

Met Leu Thr His Leu Val Asn Leu Thr Leu Ala Ala Asn Asn Phe Thr
            100                 105                 110

Gly Glu Leu Pro Leu Glu Met Lys Ser Leu Thr Ser Leu Lys Val Leu
        115                 120                 125

Asn Ile Ser Asn Asn Gly Asn Leu Thr Gly Thr Phe Pro Gly Glu Ile
    130                 135                 140

Leu Lys Ala Met Val Asp Leu Glu Val Leu Asp Thr Tyr Asn Asn Asn
145                 150                 155                 160

Phe Asn Gly Lys Leu Pro Pro Glu Met Ser Glu Leu Lys Lys Leu Lys
                165                 170                 175

Tyr Leu Ser Phe Gly Gly Asn Phe Phe Ser Gly Glu Ile Pro Glu Ser
            180                 185                 190

Tyr Gly Asp Ile Gln Ser Leu Glu Tyr Leu Gly Leu Asn Gly Ala Gly
        195                 200                 205

Leu Ser Gly Lys Ser Pro Ala Phe Leu Ser Arg Leu Lys Asn Leu Arg
    210                 215                 220

Glu Met Tyr Ile Gly Tyr Tyr Asn Ser Tyr Thr Gly Gly Val Pro Arg
```

-continued

```
225                 230                 235                 240
Glu Phe Gly Gly Leu Thr Lys Leu Glu Ile Leu Asp Met Ala Ser Cys
                245                 250                 255
Thr Leu Thr Gly Glu Ile Pro Thr Ser Leu Ser Asn Leu Lys His Leu
            260                 265                 270
His Thr Leu Phe Leu His Ile Asn Asn Leu Thr Gly His Ile Pro Pro
        275                 280                 285
Glu Leu Ser Gly Leu Val Ser Leu Lys Ser Leu Asp Leu Ser Ile Asn
    290                 295                 300
Gln Leu Thr Gly Glu Ile Pro Gln Ser Phe Ile Asn Leu Gly Asn Ile
305                 310                 315                 320
Thr Leu Ile Asn Leu Phe Arg Asn Asn Leu Tyr Gly Gln Ile Pro Glu
                325                 330                 335
Ala Ile Gly Glu Leu Pro Lys Leu Glu Val Phe Glu Val Trp Glu Asn
            340                 345                 350
Asn Phe Thr Leu Gln Leu Pro Ala Asn Leu Gly Arg Asn Gly Asn Leu
        355                 360                 365
Ile Lys Leu Asp Val Ser Asp Asn His Leu Thr Gly Leu Ile Pro Lys
    370                 375                 380
Asp Leu Cys Arg Gly Glu Lys Leu Glu Met Leu Ile Leu Ser Asn Asn
385                 390                 395                 400
Phe Phe Phe Gly Pro Ile Pro Glu Glu Leu Gly Lys Cys Lys Ser Leu
                405                 410                 415
Thr Lys Ile Arg Ile Val Lys Asn Leu Leu Asn Gly Thr Val Pro Ala
            420                 425                 430
Gly Leu Phe Asn Leu Pro Leu Val Thr Ile Ile Glu Leu Thr Asp Asn
        435                 440                 445
Phe Phe Ser Gly Glu Leu Pro Val Thr Met Ser Gly Asp Val Leu Asp
    450                 455                 460
Gln Ile Tyr Leu Ser Asn Asn Trp Phe Ser Gly Glu Ile Pro Pro Ala
465                 470                 475                 480
Ile Gly Asn Phe Pro Asn Leu Gln Thr Leu Phe Leu Asp Arg Asn Arg
                485                 490                 495
Phe Arg Gly Asn Ile Pro Arg Glu Ile Phe Glu Leu Lys His Leu Ser
            500                 505                 510
Arg Ile Asn Thr Ser Ala Asn Asn Ile Thr Gly Gly Ile Pro Asp Ser
        515                 520                 525
Ile Ser Arg Cys Ser Thr Leu Ile Ser Val Asp Leu Ser Arg Asn Arg
    530                 535                 540
Ile Asn Gly Glu Ile Pro Lys Gly Ile Asn Asn Val Lys Asn Leu Gly
545                 550                 555                 560
Thr Leu Asn Ile Ser Gly Asn Gln Leu Thr Gly Ser Ile Pro Thr Gly
                565                 570                 575
Ile Gly Asn Met Thr Ser Leu Thr Thr Leu Asp Leu Ser Phe Asn Asp
            580                 585                 590
Leu Ser Gly Arg Val Pro Leu Gly Gly Gln Phe Leu Val Phe Asn Glu
        595                 600                 605
Thr Ser Phe Ala Gly Asn Thr Tyr Leu Cys Leu Pro His Arg Val Ser
    610                 615                 620
Cys Pro Thr Arg Pro Gly Gln Thr Ser Asp His Asn His Thr Ala Leu
625                 630                 635                 640
Phe Ser Pro Ser Arg Ile Val Ile Thr Val Ile Ala Ala Ile Thr Gly
                645                 650                 655
```

-continued

```
Leu Ile Leu Ile Ser Val Ala Ile Arg Gln Met Asn Lys Lys Lys Asn
            660                 665                 670

Gln Lys Ser Leu Ala Trp Lys Leu Thr Ala Phe Gln Lys Leu Asp Phe
        675                 680                 685

Lys Ser Glu Asp Val Leu Glu Cys Leu Lys Glu Glu Asn Ile Ile Gly
    690                 695                 700

Lys Gly Gly Ser Gly Ile Val Tyr Arg Gly Ser Met Pro Asn Asn Val
705                 710                 715                 720

Asp Val Ala Ile Lys Arg Leu Val Gly Arg Gly Thr Gly Arg Ser Asp
                725                 730                 735

His Gly Phe Thr Ala Glu Ile Gln Thr Leu Gly Arg Ile Arg His Arg
            740                 745                 750

His Ile Val Arg Leu Leu Gly Tyr Val Ala Asn Lys Asp Thr Asn Leu
        755                 760                 765

Leu Leu Tyr Glu Tyr Met Pro Asn Gly Ser Leu Gly Glu Leu Leu His
    770                 775                 780

Gly Ser Lys Gly Gly His Leu Gln Trp Glu Thr Arg His Arg Val Ala
785                 790                 795                 800

Val Glu Ala Ala Lys Gly Leu Cys Tyr Leu His His Asp Cys Ser Pro
                805                 810                 815

Leu Ile Leu His Arg Asp Val Lys Ser Asn Asn Ile Leu Leu Asp Ser
            820                 825                 830

Asp Phe Glu Ala His Val Ala Asp Phe Gly Leu Ala Lys Phe Leu Val
        835                 840                 845

Asp Gly Ala Ala Ser Glu Cys Met Ser Ser Ile Ala Asp Ser Tyr Gly
    850                 855                 860

Tyr Ile Ala Pro Glu Tyr Ala Tyr Thr Leu Lys Val Asp Glu Lys Ser
865                 870                 875                 880

Asp Val Tyr Ser Phe Gly Val Val Leu Leu Glu Leu Ile Ala Gly Lys
                885                 890                 895

Lys Pro Val Gly Glu Phe Gly Glu Gly Val Asp Ile Val Arg Trp Val
            900                 905                 910

Arg Asn Thr Glu Glu Glu Ile Thr Gln Pro Ser Asp Ala Ala Ile Val
        915                 920                 925

Val Ala Ile Val Asp Pro Arg Leu Thr Gly Tyr Pro Leu Thr Ser Val
    930                 935                 940

Ile His Val Phe Lys Ile Ala Met Met Cys Val Glu Glu Glu Ala Ala
945                 950                 955                 960

Ala Arg Pro Thr Met Arg Glu Val Val His Met Leu Thr Asn Pro Pro
                965                 970                 975

Lys Ser Val Ala Asn Leu Ile Ala Phe
            980                 985
```

( 2 ) INFORMATION FOR SEQ ID NO:3:

( i ) SEQUENCE CHARACTERISTICS:
( A ) LENGTH: 523 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:3:

```
Ala Arg Val Ile Ser Leu Asn Val Ser Phe Thr Pro Leu Phe Gly Thr
1               5                   10                  15

Ile Ser Pro Glu Ile Gly Met Leu Thr His Leu Val Asn Leu Thr Leu
```

```
                20                       25                       30

Ala Ala Asn Asn Phe Thr Gly Glu Leu Pro Leu Glu Met Lys Ser Leu
        35                      40                      45

Thr Ser Leu Lys Val Leu Asn Ile Ser Asn Asn Asn Leu Thr Gly Thr
    50                      55                      60

Phe Pro Gly Glu Ile Leu Lys Ala Met Val Asp Leu Glu Val Leu Asp
65                      70                      75                      80

Thr Tyr Asn Gly Asn Asn Phe Asn Gly Lys Leu Pro Pro Glu Met Ser
                85                      90                      95

Glu Leu Lys Lys Leu Lys Tyr Leu Ser Phe Gly Gly Asn Phe Phe Ser
            100                     105                     110

Gly Glu Ile Pro Glu Ser Tyr Gly Asp Ile Gln Ser Leu Glu Tyr Leu
        115                     120                     125

Gly Leu Asn Gly Ala Gly Leu Ser Gly Lys Ser Pro Ala Phe Leu Ser
    130                     135                     140

Arg Leu Lys Asn Leu Arg Glu Met Tyr Ile Gly Tyr Tyr Asn Ser Tyr
145                     150                     155                     160

Thr Gly Gly Val Pro Arg Glu Phe Gly Gly Leu Thr Lys Leu Glu Ile
                165                     170                     175

Leu Asp Met Ala Ser Cys Thr Leu Thr Gly Glu Ile Pro Thr Ser Leu
            180                     185                     190

Ser Asn Leu Lys His Leu His Thr Leu Phe Leu His Ile Asn Asn Leu
        195                     200                     205

Thr Gly His Ile Pro Pro Glu Leu Ser Gly Leu Val Ser Leu Lys Ser
    210                     215                     220

Leu Asp Leu Ser Ile Asn Gln Leu Thr Gly Glu Ile Pro Gln Ser Phe
225                     230                     235                     240

Ile Asn Leu Gly Asn Ile Thr Leu Ile Asn Leu Phe Arg Asn Asn Leu
                245                     250                     255

Tyr Gly Gln Ile Pro Glu Ala Ile Gly Glu Leu Pro Lys Leu Glu Val
            260                     265                     270

Phe Glu Val Trp Glu Asn Asn Phe Thr Leu Gln Leu Pro Ala Asn Leu
        275                     280                     285

Gly Arg Asn Gly Asn Leu Ile Lys Leu Asp Val Ser Asp Asn His Leu
    290                     295                     300

Thr Gly Leu Ile Pro Lys Asp Leu Cys Arg Gly Glu Lys Leu Glu Met
305                     310                     315                     320

Leu Ile Leu Ser Asn Asn Phe Phe Phe Gly Pro Ile Pro Glu Glu Leu
                325                     330                     335

Gly Lys Cys Lys Ser Leu Thr Lys Ile Arg Ile Val Lys Asn Leu Leu
            340                     345                     350

Asn Gly Thr Val Pro Ala Gly Leu Phe Asn Leu Pro Leu Val Thr Ile
        355                     360                     365

Ile Glu Leu Thr Asp Asn Phe Phe Ser Gly Glu Leu Pro Val Thr Met
    370                     375                     380

Ser Gly Asp Val Leu Asp Gln Ile Tyr Leu Ser Asn Asn Trp Phe Ser
385                     390                     395                     400

Gly Glu Ile Pro Pro Ala Ile Gly Asn Phe Pro Asn Leu Gln Thr Leu
                405                     410                     415

Phe Leu Asp Arg Asn Arg Phe Arg Gly Asn Ile Pro Arg Glu Ile Phe
            420                     425                     430

Glu Leu Lys His Leu Ser Arg Ile Asn Thr Ser Ala Asn Asn Ile Thr
        435                     440                     445
```

```
Gly Gly Ile Pro Asp Ser Ile Ser Arg Cys Ser Thr Leu Ile Ser Val
    450                 455                 460

Asp Leu Ser Arg Asn Arg Ile Asn Gly Glu Ile Pro Lys Gly Ile Asn
465                 470                 475                 480

Asn Val Lys Asn Leu Gly Thr Leu Asn Ile Ser Gly Asn Gln Leu Thr
                485                 490                 495

Gly Ser Ile Pro Thr Gly Ile Gly Asn Met Thr Ser Leu Thr Thr Leu
            500                 505                 510

Asp Leu Ser Phe Asn Asp Leu Ser Gly Arg Val
        515                 520
```

( 2 ) INFORMATION FOR SEQ ID NO:4:

( i ) SEQUENCE CHARACTERISTICS:
( A ) LENGTH: 282 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:4:

```
Gly Lys Gly Gly Ser Gly Ile Val Tyr Arg Gly Ser Met Pro Asn Asn
1               5                   10                  15

Val Asp Val Ala Ile Lys Arg Leu Val Gly Arg Gly Thr Gly Arg Ser
            20                  25                  30

Asp His Gly Phe Thr Ala Glu Ile Gln Thr Leu Gly Arg Ile Arg His
        35                  40                  45

Arg His Ile Val Arg Leu Leu Gly Tyr Val Ala Asn Lys Asp Thr Asn
    50                  55                  60

Leu Leu Leu Tyr Glu Tyr Met Pro Asn Gly Ser Leu Gly Glu Leu Leu
65                  70                  75                  80

His Gly Ser Lys Gly Gly His Leu Gln Trp Glu Thr Arg His Arg Val
                85                  90                  95

Ala Val Glu Ala Ala Lys Gly Leu Cys Tyr Leu His His Asp Cys Ser
            100                 105                 110

Pro Leu Ile Leu His Arg Asp Val Lys Ser Asn Asn Ile Leu Leu Asp
        115                 120                 125

Ser Asp Phe Glu Ala His Val Ala Asp Phe Gly Leu Ala Lys Phe Leu
    130                 135                 140

Val Asp Gly Ala Ala Ser Glu Cys Met Ser Ser Ile Ala Gly Ser Tyr
145                 150                 155                 160

Gly Tyr Ile Ala Pro Glu Tyr Ala Tyr Thr Leu Lys Val Asp Glu Lys
                165                 170                 175

Ser Asp Val Tyr Ser Phe Gly Val Val Leu Leu Glu Leu Ile Ala Gly
            180                 185                 190

Lys Lys Pro Val Gly Glu Phe Gly Glu Gly Val Asp Ile Val Arg Trp
        195                 200                 205

Val Arg Asn Thr Glu Glu Glu Ile Thr Gln Pro Ser Asp Ala Ala Ile
    210                 215                 220

Val Val Ala Ile Val Asp Pro Arg Leu Thr Gly Tyr Pro Leu Thr Ser
225                 230                 235                 240

Val Ile His Val Phe Lys Ile Ala Met Met Cys Val Glu Glu Glu Ala
                245                 250                 255

Ala Ala Arg Pro Thr Met Arg Glu Val Val His Met Leu Thr Asn Pro
            260                 265                 270

Pro Lys Ser Val Ala Asn Leu Ile Ala Phe
```

275 280

( 2 ) INFORMATION FOR SEQ ID NO:5:

( i ) SEQUENCE CHARACTERISTICS:
( A ) LENGTH: 999 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:5:

```
Met Leu Tyr Cys Leu Ile Leu Leu Leu Cys Leu Ser Ser Thr Tyr Leu
1               5                   10                  15

Pro Ser Leu Ser Leu Asn Gln Asp Ala Thr Ile Leu Arg Gln Ala Lys
            20                  25                  30

Leu Gly Leu Ser Asp Pro Ala Gln Ser Leu Ser Ser Trp Ser Asp Asn
        35                  40                  45

Asn Asp Val Thr Pro Cys Lys Trp Leu Gly Val Ser Cys Asp Ala Thr
    50                  55                  60

Ser Asn Val Val Ser Val Asp Leu Ser Ser Phe Met Leu Val Gly Pro
65                  70                  75                  80

Phe Pro Ser Ile Leu Cys His Leu Pro Ser Leu His Ser Leu Ser Leu
                85                  90                  95

Tyr Asn Asn Ser Ile Asn Gly Ser Leu Ser Ala Asp Asp Phe Asp Thr
            100                 105                 110

Cys His Asn Leu Ile Ser Leu Asp Leu Ser Glu Asn Leu Leu Val Gly
        115                 120                 125

Ser Ile Pro Lys Ser Leu Pro Phe Asn Leu Pro Asn Leu Lys Phe Leu
    130                 135                 140

Glu Ile Ser Gly Asn Asn Leu Ser Asp Thr Ile Pro Ser Ser Phe Gly
145                 150                 155                 160

Glu Phe Arg Lys Leu Glu Ser Leu Asn Leu Ala Gly Asn Phe Leu Ser
                165                 170                 175

Gly Thr Ile Pro Ala Ser Leu Gly Asn Val Thr Thr Leu Lys Glu Leu
            180                 185                 190

Lys Leu Ala Tyr Asn Leu Phe Ser Pro Ser Gln Ile Pro Ser Gln Leu
        195                 200                 205

Gly Asn Leu Thr Glu Leu Gln Val Leu Trp Leu Ala Gly Cys Asn Leu
    210                 215                 220

Val Gly Pro Ile Pro Pro Ser Leu Ser Arg Leu Thr Ser Leu Val Asn
225                 230                 235                 240

Leu Asp Leu Thr Phe Asn Gln Leu Thr Gly Ser Ile Pro Ser Trp Ile
                245                 250                 255

Thr Gln Leu Lys Thr Val Glu Gln Ile Glu Leu Phe Asn Asn Ser Phe
            260                 265                 270

Ser Gly Glu Leu Pro Glu Ser Met Gly Asn Met Thr Thr Leu Lys Arg
        275                 280                 285

Phe Asp Ala Ser Met Asn Lys Leu Thr Gly Lys Ile Pro Asp Asn Leu
    290                 295                 300

Asn Leu Leu Asn Leu Glu Ser Leu Asn Leu Phe Glu Asn Met Leu Glu
305                 310                 315                 320

Gly Pro Leu Pro Glu Ser Ile Thr Arg Ser Lys Thr Leu Ser Glu Leu
                325                 330                 335

Lys Leu Phe Asn Asn Arg Leu Thr Gly Val Leu Pro Ser Gln Leu Gly
            340                 345                 350
```

-continued

```
Ala Asn Ser Pro Leu Gln Tyr Val Asp Leu Ser Tyr Asn Arg Phe Ser
        355                 360                 365

Gly Glu Ile Pro Ala Asn Val Cys Gly Glu Gly Lys Leu Glu Tyr Leu
    370                 375                 380

Ile Leu Ile Asp Asn Ser Phe Ser Gly Glu Ile Ser Asn Asn Leu Gly
385                 390                 395                 400

Lys Cys Lys Ser Leu Thr Arg Val Arg Leu Ser Asn Asn Lys Leu Ser
                405                 410                 415

Gly Gln Ile Pro His Gly Phe Trp Gly Leu Pro Arg Leu Ser Leu Leu
            420                 425                 430

Glu Leu Ser Asp Asn Ser Phe Thr Gly Ser Ile Pro Lys Thr Ile Ile
        435                 440                 445

Gly Ala Lys Asn Leu Ser Asn Leu Arg Ile Ser Lys Asn Arg Phe Ser
    450                 455                 460

Gly Ser Ile Pro Asn Glu Ile Gly Ser Leu Asn Gly Ile Ile Glu Ile
465                 470                 475                 480

Ser Gly Ala Glu Asn Asp Phe Ser Gly Glu Ile Pro Glu Ser Leu Val
                485                 490                 495

Lys Leu Lys Gln Leu Ser Arg Leu Asp Leu Ser Lys Asn Gln Leu Ser
            500                 505                 510

Gly Glu Ile Pro Arg Glu Leu Arg Gly Trp Lys Asn Leu Asn Glu Leu
        515                 520                 525

Asn Leu Ala Asn Asn His Leu Ser Gly Glu Ile Pro Lys Glu Val Gly
    530                 535                 540

Ile Leu Pro Val Leu Asn Tyr Leu Asp Leu Ser Ser Asn Gln Phe Ser
545                 550                 555                 560

Gly Glu Ile Pro Leu Glu Leu Gln Asn Leu Lys Leu Asn Val Leu Asn
                565                 570                 575

Leu Ser Tyr Asn His Leu Ser Gly Lys Ile Pro Pro Leu Tyr Ala Asn
            580                 585                 590

Lys Ile Tyr Ala His Asp Phe Ile Gly Asn Pro Gly Leu Cys Val Asp
        595                 600                 605

Leu Asp Gly Leu Cys Arg Lys Ile Thr Arg Ser Lys Asn Ile Gly Tyr
    610                 615                 620

Val Trp Ile Leu Leu Thr Ile Phe Leu Leu Ala Gly Leu Val Phe Val
625                 630                 635                 640

Val Gly Ile Val Met Phe Ile Ala Lys Cys Arg Lys Leu Arg Ala Leu
                645                 650                 655

Lys Ser Ser Thr Leu Ala Ala Ser Lys Trp Arg Ser Phe His Lys Leu
            660                 665                 670

His Phe Ser Glu His Glu Ile Ala Asp Cys Leu Asp Glu Lys Asn Val
        675                 680                 685

Ile Gly Phe Gly Ser Ser Gly Lys Val Tyr Lys Val Glu Leu Arg Gly
    690                 695                 700

Gly Glu Val Val Ala Val Lys Lys Leu Asn Lys Ser Val Lys Gly Gly
705                 710                 715                 720

Asp Asp Glu Tyr Ser Ser Asp Ser Leu Asn Arg Asp Val Phe Ala Ala
                725                 730                 735

Glu Val Glu Thr Leu Gly Thr Ile Arg His Lys Ser Ile Val Arg Leu
            740                 745                 750

Trp Cys Cys Cys Ser Ser Gly Asp Cys Lys Leu Leu Val Tyr Glu Tyr
        755                 760                 765

Met Pro Asn Gly Ser Leu Ala Asp Val Leu His Gly Asp Arg Lys Gly
```

770 775 780

Gly Val Val Leu Gly Trp Pro Glu Arg Leu Arg Ile Ala Leu Asp Ala
785 790 795 800

Ala Glu Gly Leu Ser Tyr Leu His His Asp Cys Val Pro Pro Ile Val
805 810 815

His Arg Asp Val Lys Ser Ser Asn Ile Leu Leu Asp Ser Asp Tyr Gly
820 825 830

Ala Lys Val Ala Asp Phe Gly Ile Ala Lys Val Gly Gln Met Ser Gly
835 840 845

Ser Lys Thr Pro Glu Ala Met Ser Gly Ile Ala Gly Ser Cys Gly Tyr
850 855 860

Ile Ala Pro Glu Tyr Val Tyr Thr Leu Arg Val Asn Glu Lys Ser Asp
865 870 875 880

Ile Tyr Ser Phe Gly Val Val Leu Leu Glu Leu Val Thr Gly Lys Gln
885 890 895

Pro Thr Asp Ser Glu Leu Gly Asp Lys Asp Met Ala Lys Trp Val Cys
900 905 910

Thr Ala Leu Asp Lys Cys Gly Leu Glu Pro Val Ile Asp Pro Lys Leu
915 920 925

Asp Leu Lys Phe Lys Glu Glu Ile Ser Lys Val Ile His Ile Gly Leu
930 935 940

Leu Cys Thr Ser Pro Leu Pro Leu Asn Arg Pro Ser Met Arg Lys Val
945 950 955 960

Val Ile Met Leu Gln Glu Val Ser Gly Ala Val Pro Cys Ser Ser Pro
965 970 975

Asn Thr Ser Lys Arg Ser Lys Thr Gly Gly Lys Leu Ser Pro Tyr Tyr
980 985 990

Thr Glu Asp Leu Asn Ser Val
995

( 2 ) INFORMATION FOR SEQ ID NO:6:

( i ) SEQUENCE CHARACTERISTICS:
( A ) LENGTH: 980 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:6:

Met Ala Met Arg Leu Leu Lys Thr His Leu Leu Phe Leu His Leu Tyr
1 5 10 15

Leu Phe Phe Ser Pro Cys Phe Ala Tyr Thr Asp Met Glu Val Leu Leu
20 25 30

Asn Leu Lys Ser Ser Met Ile Gly Pro Lys Gly His Gly Leu His Asp
35 40 45

Trp Ile His Ser Ser Ser Pro Asp Ala His Cys Ser Phe Ser Gly Val
50 55 60

Ser Cys Asp Asp Asp Ala Arg Val Ile Ser Leu Asn Val Ser Phe Thr
65 70 75 80

Pro Leu Phe Gly Thr Ile Ser Pro Glu Ile Gly Met Leu Thr His Leu
85 90 95

Val Asn Leu Thr Leu Ala Ala Asn Asn Phe Thr Gly Glu Leu Pro Leu
100 105 110

Glu Met Lys Ser Leu Thr Ser Leu Lys Val Leu Asn Ile Ser Asn Asn
115 120 125

Gly Asn Leu Thr Gly Thr Phe Pro Gly Glu Ile Leu Lys Ala Met Val
130 135 140

Asp Leu Glu Val Leu Asp Thr Tyr Asn Asn Asn Phe Asn Gly Lys Leu
145 150 155 160

Pro Pro Glu Met Ser Glu Leu Lys Lys Leu Lys Tyr Leu Ser Phe Gly
165 170 175

Gly Asn Phe Phe Ser Gly Glu Ile Pro Glu Ser Tyr Gly Asp Ile Gln
180 185 190

Ser Leu Glu Tyr Leu Gly Leu Asn Gly Ala Gly Leu Ser Gly Lys Ser
195 200 205

Pro Ala Phe Leu Ser Arg Leu Lys Asn Leu Arg Glu Met Tyr Ile Gly
210 215 220

Tyr Tyr Asn Ser Tyr Thr Gly Gly Val Pro Arg Glu Phe Gly Gly Leu
225 230 235 240

Thr Lys Leu Glu Ile Leu Asp Met Ala Ser Cys Thr Leu Thr Gly Glu
245 250 255

Ile Pro Thr Ser Leu Ser Asn Leu Lys His Leu His Thr Leu Phe Leu
260 265 270

His Ile Asn Asn Leu Thr Gly His Ile Pro Pro Glu Leu Ser Gly Leu
275 280 285

Val Ser Leu Lys Ser Leu Asp Leu Ser Ile Asn Gln Leu Thr Gly Glu
290 295 300

Ile Pro Gln Ser Phe Ile Asn Leu Gly Asn Ile Thr Leu Ile Asn Leu
305 310 315 320

Phe Arg Asn Asn Leu Tyr Gly Gln Ile Pro Glu Ala Ile Gly Glu Leu
325 330 335

Pro Lys Leu Glu Val Phe Glu Val Trp Glu Asn Asn Phe Thr Leu Gln
340 345 350

Leu Pro Ala Asn Leu Gly Arg Asn Gly Asn Leu Ile Lys Leu Asp Val
355 360 365

Ser Asp Asn His Leu Thr Gly Leu Ile Pro Lys Asp Leu Cys Arg Gly
370 375 380

Glu Lys Leu Glu Met Leu Ile Leu Ser Asn Asn Phe Phe Phe Gly Pro
385 390 395 400

Ile Pro Glu Glu Leu Gly Lys Cys Lys Ser Leu Thr Lys Ile Arg Ile
405 410 415

Val Lys Asn Leu Leu Asn Gly Thr Val Pro Ala Gly Leu Phe Asn Leu
420 425 430

Pro Leu Val Thr Ile Ile Glu Leu Thr Asp Asn Phe Phe Ser Gly Glu
435 440 445

Leu Pro Val Thr Met Ser Gly Asp Val Leu Asp Gln Ile Tyr Leu Ser
450 455 460

Asn Asn Trp Phe Ser Gly Glu Ile Pro Pro Ala Ile Gly Asn Phe Pro
465 470 475 480

Asn Leu Gln Thr Leu Phe Leu Asp Arg Asn Arg Phe Arg Gly Asn Ile
485 490 495

Pro Arg Glu Ile Phe Glu Leu Lys His Leu Ser Arg Ile Asn Thr Ser
500 505 510

Ala Asn Asn Ile Thr Gly Gly Ile Pro Asp Ser Ile Ser Arg Cys Ser
515 520 525

Thr Leu Ile Ser Val Asp Leu Ser Arg Asn Arg Ile Asn Gly Glu Ile
530 535 540

Pro Lys Gly Ile Asn Asn Val Lys Asn Leu Gly Thr Leu Asn Ile Ser

-continued 545 550 555 560

Gly Asn Gln Leu Thr Gly Ser Ile Pro Thr Gly Ile Gly Asn Met Thr
565 570 575

Ser Leu Thr Thr Leu Asp Leu Ser Phe Asn Asp Leu Ser Gly Arg Val
580 585 590

Pro Leu Gly Gly Gln Phe Leu Val Phe Asn Glu Thr Ser Phe Ala Gly
595 600 605

Asn Thr Tyr Leu Cys Leu Pro His Arg Val Ser Cys Pro Thr Arg Pro
610 615 620

Gly Gln Thr Ser Asp His Asn His Thr Ala Leu Phe Ser Pro Ser Arg
625 630 635 640

Ile Val Ile Thr Val Ile Ala Ala Ile Thr Gly Leu Ile Leu Ile Ser
645 650 655

Val Ala Ile Arg Gln Met Asn Lys Lys Lys Asn Gln Lys Ser Leu Ala
660 665 670

Trp Lys Leu Thr Ala Phe Gln Lys Leu Asp Phe Lys Ser Glu Asp Val
675 680 685

Leu Glu Cys Leu Lys Glu Glu Asn Ile Ile Gly Lys Gly Gly Ser Gly
690 695 700

Ile Val Tyr Arg Gly Ser Met Pro Asn Asn Val Asp Val Ala Ile Lys
705 710 715 720

Arg Leu Val Gly Arg Gly Thr Gly Arg Ser Asp His Gly Phe Thr Ala
725 730 735

Glu Ile Gln Thr Leu Gly Arg Ile Arg His Arg His Ile Val Arg Leu
740 745 750

Leu Gly Tyr Val Ala Asn Lys Asp Thr Asn Leu Leu Leu Tyr Glu Tyr
755 760 765

Met Pro Asn Gly Ser Leu Gly Glu Leu Leu His Gly Ser Lys Gly Gly
770 775 780

His Leu Gln Trp Glu Thr Arg His Arg Val Ala Val Glu Ala Ala Lys
785 790 795 800

Gly Leu Cys Tyr Leu His His Asp Cys Ser Pro Leu Ile Leu His Arg
805 810 815

Asp Val Lys Ser Asn Asn Ile Leu Leu Asp Ser Asp Phe Glu Ala His
820 825 830

Val Ala Asp Phe Gly Leu Ala Lys Phe Leu Val Asp Gly Ala Ala Ser
835 840 845

Glu Cys Met Ser Ser Ile Ala Gly Ser Tyr Gly Tyr Ile Ala Pro Glu
850 855 860

Tyr Ala Tyr Thr Leu Lys Val Asp Glu Lys Ser Asp Val Tyr Ser Phe
865 870 875 880

Gly Val Val Leu Leu Glu Leu Ile Ala Gly Lys Lys Pro Val Gly Glu
885 890 895

Phe Gly Glu Gly Val Asp Ile Val Arg Trp Val Arg Asn Thr Glu Glu
900 905 910

Glu Ile Thr Gln Pro Ser Asp Ala Ala Ile Val Val Ala Ile Val Asp
915 920 925

Pro Arg Leu Thr Gly Tyr Pro Leu Thr Ser Val Ile His Val Phe Lys
930 935 940

Ile Ala Met Met Cys Val Glu Glu Glu Ala Ala Ala Arg Pro Thr Met
945 950 955 960

Arg Glu Val Val His Met Leu Thr Asn Pro Pro Lys Ser Val Ala Asn
965 970 975

Leu Ile Ala Phe
980

(2) INFORMATION FOR SEQ ID NO:7:

(i) SEQUENCE CHARACTERISTICS:
(A) LENGTH: 336 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:7:

```
CGCTCTTTCT CACTGAGAGG ACACTAAAAA AATGGCGATG AGACTTTTGA AGACTCATCT     60
TCTGTTTCTG CATCTGTATC TATTTTTCTC ACCATGTTTC GCTTACACTG ACATGGAAGT    120
TCTTCTCAAT CTCAAATCCT CCATGATTGG TCCTAAAGGA CACGGTCTCC ACGACTGGAT    180
TCACTCATCT TCTCCGGATG CTCACTGTTC TTTCTCCGGC GTCTCATGTG ACGACGATGC    240
TCGTGTTATC TCTCTCAACG TCTCCTTCAC TCCTTTGTTT GGTACAATCT CACCAGAGAT    300
TGGGATGTTG ACTCATTTGG TGAATCTAAC TTTAGC                              336
```

(2) INFORMATION FOR SEQ ID NO:8:

(i) SEQUENCE CHARACTERISTICS:
(A) LENGTH: 318 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:8:

```
CGGAGTGGTT TTGTTGGAGT TAATAGCTGG GAAGAAACCT GTTGGTGAAT TTGGAGAAGG     60
AGTGGATATA GTTAGGTGGG TGAGGAACAC GGAAGAGGAG ATAACTCAGC CATCGGATGC    120
TGCTATTGTT GTTGCGATTG TTGACCCGAG GTTGACTGGT TACCCGTTGA CAAGTGTGAT    180
TCATGTGTTC AAGATCGCAA TGATGTGTGT GGAGGAAGAA GCCGCGGCAA GGCCTACGAT    240
GAGGGAAGTT GTGCACATGC TCACTAACCC TCCTAAATCC GTGGCGAACT TGATCGCGTT    300
CTGACCCAAG CAAGATAA                                                  318
```

(2) INFORMATION FOR SEQ ID NO:9:

(i) SEQUENCE CHARACTERISTICS:
(A) LENGTH: 24 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:9:

```
Pro Xaa Xaa Leu Xaa Xaa Leu Xaa Xaa Leu Xaa Xaa Leu Xaa Leu Xaa
1               5                   10                  15
Xaa Asn Xaa Xaa Ser Gly Xaa Ile
            20
```

(2) INFORMATION FOR SEQ ID NO:10:

(i) SEQUENCE CHARACTERISTICS:
(A) LENGTH: 8 amino acids
(B) TYPE: amino acid
(C) STRANDEDNESS: unknown
(D) TOPOLOGY: unknown -continued ( i i ) MOLECULE TYPE: protein ( x i ) SEQUENCE DESCRIPTION: SEQ ID NO:10:

```
Gly Ala Gly Leu Ser Gly Lys Ser
1               5
```

( 2 ) INFORMATION FOR SEQ ID NO:11:

( i ) SEQUENCE CHARACTERISTICS:
( A ) LENGTH: 8 amino acids
( B ) TYPE: amino acid
( C ) STRANDEDNESS: unknown
( D ) TOPOLOGY: unknown ( i i ) MOLECULE TYPE: protein ( i x ) FEATURE:
( A ) NAME/KEY: Modified-site
( B ) LOCATION: 8
( D ) OTHER INFORMATION: /note= "The amino acid located at position 8 can either be Serine or Threonine."

( x i ) SEQUENCE DESCRIPTION: SEQ ID NO:11:

```
Gly Xaa Xaa Xaa Xaa Gly Lys Xaa
1               5
```

PLANT CLAVATA1 NUCLEIC ACIDS, TRANSFORMED PLANTS, AND PROTEINS

The U.S. Government has certain rights in this invention pursuant to grant number MCB 9204839 from the National Science Foundation.

FIELD OF THE INVENTION

The invention generally relates to clavata1 nucleic acids, proteins, and antibodies, and to plants transformed with clavata1 nucleic acids having altered phenotypes.

BACKGROUND OF THE INVENTION

Meristems are central to higher plant development, as almost all post-embryonic organs, including roots, leaves, flowers and axillary meristems, are initiated by either shoot or root meristems. Two aspects of shoot meristem development are central to its function. First, the meristem must maintain a group of cells in the center that remain undifferentiated. The proliferation of these undifferentiated meristem cells is necessary to provide new cells for organ initiation. In Arabidopsis, for example, new organs are generated throughout the life span, requiring the plant to maintain a pool of undifferentiated cells from which to draw for organ and new meristem initiation. Second, as the meristem apex moves away from these undifferentiated cells by continuted cell division, the undifferentiated cells that are now on the flanks of the meristem must be allowed to enter a specific developmental pathway, such as leaf or flower development, leading to eventual differentiation. It is the balancing of these two features that allows for the continued growth of the meristem and its continuous initiation of new organs.

Proliferation of meristem cells balanced with their subsequent incorporation into organ primordia relates to the classical separation of the shoot meristem into a central zone (CZ) and surrounding peripheral zone (PZ). The CZ at the very tip of the shoot meristem, would correspond to the region where cells are maintained in an undifferentiated state. In the PZ, daughter cells enter a specific developmental pathway and become incorporated into organ primordia. Molecular evidence corroborates this distinction. A number of mutants that disrupt meristem development have been described in Arabidopsis.

The existence of CLAVATA1 is well known in *Arabidopsis thaliana.* It was identified through the phenotype of its mutant alleles, best described in Clark et al., Development 119: 397–418 (1993); see also Koomneef et al., J. Hered. 74: 265–272 (1983); Bowman et al., Oxford Rev. Plant Cell & Mol. Biol. 5: 57–87 (1988); and Leyser et al., Development 116: 397–403 (1992). The gene has also been described under the names FLO5, FAS3 and FUF by rediscoverers, between the time when they found new alleles, and the time when it was shown that they had identified alleles of the earlier-described CLAVATA1 gene.

Mutations in the gene cause a loss of normal control of cell division in shoot apical meristems and in floral meristems. The result of loss of cell division control is in either case an enlargement of the meristem. In shoot apical meristems this enlargement can lead to fasciation (cresting), where the meristem grows very large, causing the stem to become straplike, and leaves and flowers to be produced in great profusion. In flowers the enlargement leads to an increase in the number of floral organs, including an increase in carpel number, which increases fruit size and seed number.

There are naturally occurring mutations whose phenotypes resemble those of CLAVATA1 in Arabidopsis. Celosia, or cock's comb, is a cultivated flowering plant that differs from its wild progenitors by fasciation, which enlarges the inflorescence. Since the inflorescence leaves (bracts) are the colorful part, the cultivated variety is much showier than the wild ones. Crested cactuses and other succulents also are considered highly desirable, but as cresting occurs in cactus as a rare response to unknown environmental conditions, the commercial crested cactuses are not genetic variants. Similarly, wild tomatoes are small berries with two carpels, or fruit components. The large, beefsteak-type cultivated tomatoes are mutants in a gene that gives extra floral organs, similar to CLAVATA1 mutants. The organs of interest are carpels, which are increased to about 6 in number, giving a much larger fruit.

A separate locus, CLAVATA2, appears to exhibit similar mutant phenotypes based on brief descriptions (McKelvie, Radiation Botany 1: 233–241 (1962); Koomneef et al., J. Hered. 74: 265–272 (1983)).

Thus, it would be desirable to be able to control the size and appearance of shoot and floral meristems, to give increased yields of leaves, flowers, and fruit. Accordingly, it is an object of the invention to provide for clavata1 nucleic acids and proteins, and modified clavata1 nucleic acids and proteins which result in altered meristem phenotypes.

It is a further object to provide plant cells and plants which contain the recombinant clavata1 nucleic acids and proteins of the invention.

SUMMARY OF THE INVENTION

In accordance with the foregoing objects, the invention provides recombinant nucleic acids encoding a clavata1 protein, and modified clavata1 nucleic acids encoding a modified clavata1 protein containing the substitution, insertion or deletion of one or more amino acids of a clavata1 protein. The substitution, insertion or deletion alters the clavata1 phenotype, preferably by decreasing the clavata1 activity resulting in an enlargement of at least one shoot apical meristem or floral meristem.

Also provided are anti-sense clavata1 nucleic acids.

A further aspect of the invention provides recombinant nucleic acids comprising a promoter operably linked to a modified clavata1 nucleic acid. The promoter is capable of causing expression of the modified clavata1 nucleic acid in a plant cell. Expression vectors are also provided which comprise transcriptional and translational regulatory DNA operably linked to DNA encoding a clavata1 protein.

An additional aspect of the invention provides plant cells transformed with an expression vector comprising a nucleic acid encoding a clavata1 protein, and plants comprising these plant cells. These plants may have a phenotype characterized by the enlargement of at least one meristem of the plant.

Methods are also provided for producing a plant having at least one transformed plant cell and a phenotype characterized by the enlargement of at least one meristem of the plant. The method comprises the steps of:

a) transforming at least one plant cell with a modified clavata1 nucleic acid;

b) regenerating plants from one or more of said transformed plant cells; and c) selecting at least one plant having said phenotype.

Seeds from the transformed plants are also provided.

In a further aspect, the invention provides recombinant clavata1 proteins, and monoclonal antibodies generated to a clavata1 protein.

BRIEF DESCRIPTION OF THE DRAWINGS

FIG. 1 depicts the genetic map for chromosome 1 of *Arabidopsis thaliana* listing some visible markers and their relative positions. The CLV1 gene is in bold type.

FIG. 2 depicts a map of RFLP clones relative to CLV1. The number of recombinants between markers and CLV1 are given. A single YAC, D6, hybridizing to m532, m237 and g6838 is shown.

FIG. 3 depicts fine scale mapping of several cosmids relative to CLV1. The numbers beneath the cosmids depict the frequency of recombination between cosmid-derived RFLP probes and CLV1.

FIG. 4 depicts a physical map of cosT. Small vertical hash bars represent HindIII restriction sites. Four genes are shown. Two of the genes (VPS-35 and RHO) lie distal to the HindIII fragment containing the recombination breakpoint. The sequenced regions are indicated.

FIGS. 5A–5H depict the complete genomic nucleic acid (SEQ ID NO:1) and amino acid sequence (SEQ ID NO:2) of clavata1 from *Arabidopsis thaliana.* The 5733 base fragment containing CLV1 is shown. Stop codons are indicated with an asterisk. Note the intron starting at nucleotide number 5029 extending through nucleotide number 5116.

FIGS. 6A and 6B depict the leucine-rich repeat (LRR) (SEQ ID NO:3) and kinase domains (SEQ ID NO:4) of clavata1. FIG. 6A shows an alignment of repeats of the LRR domain. Amino acids corresponding to residues 70 to 592 are shown. The 21 complete LRRs and one partial repeat are aligned, with a consensus sequence shown below in bold. FIG. 6B shows the kinase domain. Highly conserved residues for ser/thr kinase are shown in bold, those for tyr kinases are underlined (those residues underlined and bold are found in both). When the LRR-kinase sequence diverges from the consensus sequence, the consensus sequence (SEQ ID NOS:3 and 4) is shown below.

FIG. 7 depicts the nucleotide base changes identified in the clv1 mutant alleles. Position refers to the amino acid number starting at the N-terminal methionine (M) as 1 and ending at the C-terminal phenylalanine (F) as 980.

FIGS. 8A and 8B depict the GAP alignment between the RLK5 protein (bottom) (SEQ ID NO:5) and the CLV1 protein (top) (SEQ ID NO:6). Identical residues are indicated with an asterisk, similar residues with a dot, and gaps are indicated with dashes. Residues altered in clv1 mutants are shown in bold, and the CLV1-specific nucleotide binding site (NBS) motif is underlined.

FIGS. 9A (SEQ ID NO:7) and 9B (SEQ ID NO:8) depicts the sequence of two particular CLV1 gene specific regions. FIG. 9A: T11R1/R4 (SEQ ID NO:7) is 336 base pairs in length and spans 31 bases of the 5' untranslated region and the first 305 bases of the open reading frame (ORF). FIG. 9B: BW4/KD4 (SEQ ID NO:8) is 318 bases long and covers the last 301 bases of the ORF and 18 bases of the 3' untranslated region.

FIG. 10 is a schematic diagram of the protein coded for by CLV1. Boxes corresponding to the signal peptide, each of the 21 leucine rich repeats, and the transmembrane domain, and the kinase domain are indicated. Below the diagram, the changes identified in the mutant genomes are shown. For example, G>>E for clv1-4 indicates that the sequence coding for glycine in the wild-type genome is altered to code for glutamic acid in the mutant genome.

DETAILED DESCRIPTION OF THE INVENTION

The invention provides, in part, clavata1 nucleic acids and proteins, and plants containing such nucleic acids and proteins. Such transformed plants have altered meristem phenotypes. In a preferred embodiment, the eclavata1 nucleic acids and proteins are from Arabidopsis, preferably *A. thaliana.* However, using the techniques outlined below, clavata1 nucleic acids and proteins from other plants may also be obtained.

A clavata1 plant protein may be identified in several ways. In one embodiment, a clavata1 nucleic acid or clavata1 protein is initially identified by substantial nucleic acid and/or amino acid sequence homology to the sequences shown in FIG. 5 (SEQ ID NOS:1 and 2), as described below. Such homology can be based upon the overall nucleic acid or amino acid sequence homology.

It is to be understood that the clavata1 proteins of the present invention have a number of functional domains identified via sequence homology to known genes, and thus there may be localized areas within the clavata1 protein which have higher homologies to other proteins within these limited areas. These functional domains include a signal peptide, leucine-rich repeats (LRRs), a nucleotide binding site (NBS), a transmembrane domain and a kinase domain, each described below.

The amino terminus of the clavata1 protein shown in FIG. 5 (SEQ ID NO:2) codes for a stretch of amino acids that meet the criterion of a signal peptide (see von Heijne, Biochim. Biophys. Acta 947: 307–333 (1988)), including the conserved n-, h- and c-regions. The n-region can be from 1–20 residues and has an overall positive charge. The n-region of the clavata1 protein shown in FIG. 5 (SEQ ID NO:2) has a net charge of +2. This is followed by the h-region that is usually rich in apolar residues (i.e. Phe, Ile, Leu, Met, Val or Trp). For the clavata1 protein of FIG. 5 (SEQ ID NO:2), 9 of 11 residues in the putative h-region are apolar. The border between the h-region and the following c-region is often proline, glycine, glutamine, serine or a charged residue. The clavata1 protein of FIG. 5 (SEQ ID NO:2) has a proline as a border residue. In addition, border residues are often at position −5 or −6 from the cleavage site, with position −3 occupied by a small uncharged residue, position −2 by a large bulky residue or charged residue, with the −1 residue being small and uncharged. In the clavata1 protein of FIG. 5 (SEQ ID NO:2), the border proline residue is at −6, an alanine at −3, a tyrosine at −2, and a threonine at −1.

The clavata1 proteins of the invention also have limited sequence homology to a class of transmembrane protein kinases with a characteristic amino acid repeat called a "leucine rich repeat" (LRR). LRRs are though to play a role either as receptors or in protein-protein interactions. Other members of this class are plant genes of unknown function such as RLK5 and TMK1 of Arabidopsis (Chang et al., Plant Cell 4: 1263–1271 (1992), Walker, Plant J. 3: 451–456 (1993)), pathogen resistance genes in plants (Bent et al., Science 265: 1856–1860 (1994); Whitham et al., Cell 78: 1101–1115 (1994)), Toll of Drosophila (Hashimoto et al., Cell 52: 269–279 (1988)), and the insulin-like growth factor binding protein in mammals (Dai and Baxter, Biochem. Biophys. Res. Comm. 188: 304–309 (1992). The Toll gene is a well-studied example which functions in establishing the dorsal-ventral polarity of fly embryos. This function is induced by the extracellular interaction of a peptide ligand with the Toll transmembrane receptor, which then transmits a signal that leads to nuclear localization of the Dorsal protein, signaling ventral fate. Leucine rich repeats are also motifs in recently identified plant disease resistance genes, such as N of tobacco (Whitham et al., Cell 78: 1101–1115 (1994)), RPS2 of Arabidopsis (Mindrinos et al., Cell 78:

1089–1099 (1994); and Bent et al., Science 265: 1856–1860 (1994)), and Cf9 of tomato (Jones et al., Science 266: 789–793 (1994)).

The clavata1 protein shown in FIG. 5 (SEQ ID NO:2) contains 21 complete LRRs of 24 amino acids each. The LRRs are shown in FIG. 6 (SEQ ID NOS:3 and 4).

The clavata1 proteins of the invention also have a nucleotide binding site (NBS). In the clavata1 protein depicted in FIG. 5 (SEQ ID NO:2), a consensus sequence for an ATP/GTP binding domain is present in the fifth complete LRR (see Saraste et al., Trends Biochem. Sci. 15: 430–434 (1990)). As shown below, this NBS is important for biological function of the clavata1 protein, and no other known LRR domain of any known protein contains an NBS motif. This makes this NBS motif a preferred sequence for identifying other clavata1 proteins and nucleic acids, particularity from other plants.

The LRR domain is followed by a classic stop-transfer transmembrane domain (von Heijne, supra). Stop-transfer sequence generally contain an polar stretch of 20 residues, followed by a region containing positively harged residues. In clavata1, there are 19 apolar residues followed by 10 residues with a net charge of +5.

Following the transmembrane domain is a protein kinase domain, putatively located in the cytoplasm. Clavata1 contains all of the consensus residues found in serine/threonine protein kinases (Hanks et al., Methods. Enzymol. 200: 38–61 (1991)), including Gly699, Gly701, Val706, Ala718, Lys720, Glu737, Asp817, Lys819, Asn822, Asp835, Gly837, Pro863, Glu864, Asp877, Gly881, and Arg957 (See also FIG. 6 (SEQ ID NOS:3 and 4)). Clavata1 also contains many of the conserved residues found among mammalian tyrosine kinases, including Gly699, Gly701, Gly704, Val706, Ala718, Lys720, Glu737, Gly772, Leu774, Gly801, His815, Arg816, Asp817, Asn822, Asp835, Phe836, Gly837, Glu864, Ser875, Asp876, Val877, Gly881, Glu886, Pro893, Pro935, Cys949, Arg957, and Pro958 (see also FIG. 6 (SEQ ID NOS:3 and 4)).

In addition to these functional domains, it appears that there are stretches of unique sequences at the amino- and carboxy-termini of the protein and nucleic acid which encodes these portions; that is, there is little or no homology between these sequences and known proteins and nucleic acids. Specifically, it appears that the nucleic acid sequences encoding about the first 100 amino acids and about the last 100 amino acids of the clavata1 protein are unique to clavata1. These residues are thus ideal for identifying clavata1 proteins, as is more fully described below.

On the amino acid level, the clavata protein has an overall 37% homology with the RLK5 gene of Arabidopsis, a gene of unknown function in plant growth or development (Walker, supra). The RLK5 protein (SEQ ID NO:5) has 21 LRRs in the N-terminal domain and all the consensus residues of a serine/threonine kinase in the C-terminal domain. An alignment of the two coding regions is shown in FIG. 8 (SEQ ID NOS:5 and 6); the overall homology is 37% on the amino acid level and 51% identical at the nucleic acid level. The identity in the kinase region (gly699 to arg957) is 51%. The similarity in the LRR domain (Cys59 to Cys620) is 35%, but most (66%) of the identical residues are at the consensus LRR locations. RLK5 (SEQ ID NO:5) also lacks an NBS site in its LRR domain.

The clavata1 protein from Arabidopsis also has limited homology to two other Arabidopsis genes, TMK1 and TMKL1 (Chang et al., The Plant Cell 4: 1263–1271 (1992); Valon et al., Plant Mol. Biol. 23: 415–421 (1993)). Both of these genes were cloned based on their map position, and no function has been identified for either gene, although they are putatively identified as transmembrane kinases. Both have fewer LRRs, (for example, TMK1 has 11), and neither has an NBS site in their LRR domain. In addition, the TMKL1 gene lacks many of the conserved kinase residues. The overall homology of clavata1 and TMK1 is less than the homology between clavata1 (SEQ ID NO:6) and RLK5 (SEQ ID NO:5).

As used herein, a protein is a "clavata1 protein" if the overall homology of the protein sequence to the amino acid sequence shown in FIG. 5 (SEQ ID NO:2) is preferably greater than about 45–50%, more preferably greater than about 55–60% and most preferably greater than 70–75%. In some embodiments the homology will be as high as about 80 to 90 to 95 or 98%. This homology will be determined using standard techniques known in the art, such as the Best Fit sequence program described by Devereux et al., *Nucl. Acid Res.* 12: 387–395 (1984), the blastp program (National Center for Biotechnology Information), CLUSTAL V, or SeqEd (Applied Biosystems). The alignment may include the introduction of gaps in the sequences to be aligned. In addition, for sequences which contain either more or fewer amino acids than the protein shown in FIG. 5 (SEQ ID NO:2), it is understood that the percentage of homology will be determined based on the number of homologous amino acids in relation to the total number of amino acids. Thus, for example, homology of sequences shorter than that shown in FIG. 2, as discussed below, will be determined using the number of amino acids in the shorter sequence. In addition, in a preferred embodiment, homology is determined using identical rather than similar residues.

Notwithstanding the overall sequence homology, it is preferred that either the unique amino-terminal sequence or the unique carboxy-terminal sequence be used to identify a clavata1 protein. When using these sequences it is preferred that the amino acid sequence homology be greater than about 45%, more preferably about 55%, and most preferably greater than 75%. In some embodiments the homology will be as high as about 90 to 95 or 98%.

Similarly, a preferred embodiment utilizes the presence of an NBS site in the LRR region to identify a clavata1 protein, alone or in combination with (1) the above unique N- or C-terminal sequences and/or (2) the overall homology to the sequence shown in FIG. 5 (SEQ ID NO:2) as set forth above.

Clavata1 proteins of the present invention may be shorter or longer than the amino acid sequence shown in FIG. 5 (SEQ ID NO:2). Thus, in one embodiment, other clavata1 proteins are longer than the sequence depicted in FIG. 5 (SEQ ID NO:2).

In an alternative embodiment, included within the definition of clavata1 proteins are portions or fragments of the sequence shown in FIG. 5 (SEQ ID NO:2). The fragments may range from about 50 to about 900 amino acids. Fragments of at least about 100 amino acids are preferred and fragments of at least about 200 amino acids are particularly preferred. Fragments comprising the LRR domain and/or the kinase domain and/or conserved amino or carboxy terminus are particularly preferred. Fragments of the amino-terminus or carboxy-terminus may be smaller for use in generating antibodies, for example. Thus, these fragments may be at least 8 amino acids, more preferably at least 16, and most preferably at least 24 or 50 amino acids.

The fragments are identified as clavata1 proteins on the basis of homology or biological activity. Thus, a portion of the clavata1 protein may be considered a clavata1 protein if it shares at least one epitope with the full length clavata1 protein, as described below. Alternatively, the fragment may have biological activity, i.e. the ability to prevent meristem enlargement, or kinase activity.

In a preferred embodiment, when the clavata1 protein is to be used to generate antibodies, the clavata1 protein must share at least one epitope or determinant with the full length protein or the protein shown in FIG. 5 (SEQ ID NO:2). By “epitope” or “determinant” herein is meant a portion of a protein which will generate and bind an antibody. Thus, in most instances, antibodies made to a smaller clavata1 protein will be able to bind to the full length protein. In a preferred embodiment, the epitope is unique; that is, antibodies generated to a unique epitope show little or no cross-reactivity with other proteins.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequences of FIG. 5 (SEQ ID NO:2) is preferably greater than 40–45%, more preferably greater than about 50–55% and most preferably greater than 65–75%. In some embodiments the homology will be as high as about 90 to 95 or 98%.

In one embodiment, the nucleic acid homology is determined through hybridization studies. Thus, for example, nucleic acids which hybridize under high stringency to the nucleic acid sequences shown in FIG. 5 (SEQ ID NO:2) are considered clavata1 protein genes. High stringency conditions are generally 0.1 XSSC at 37°–65° C.

In another embodiment, less strigent hybridization conditions are used to identify clavata1 genes from other plants. For example, reduced stringency conditions are generally 2XSSPE at 50° C.

As for the protein sequence, in a preferred embodiment the nucleic acids encoding the amino- and carboxy-terminal unique sequences of the clavata1 protein are used to identify clavata1 nucleic acids. As shown in the Examples, probes to the nucleic acid encoding the amino-terminus and carboxy-terminus of clavata1 are clavata1 specific. In one embodiment, the probes shown in FIG. 9 (SEQ ID NOS:7 and 8) are used to identify clavata1 genes. The amino terminal probe of FIG. 9 (SEQ ID NOS:7 and 8) is 336 base pairs in length and spans 31 bases of the 5' untranslated region of the Arabidopsis clavata1 gene and the first 305 bases of the ORF. Probes which do not contain the untranslated region are preferably used to identify clavata1 genes from other plants. The carboxy terminal probe of FIG. 9 (SEQ ID NOS:7 and 8) is 318 basepairs in length and covers last 301 bases of the ORF and 17 bases of the 3' untranslated region. Similarly, probes which do not contain the untranslated region are preferably used to identify clavata1 genes from other plants.

Functional assays may also aid in the identification of clavata1 nucleic acids. Clavata1 nucleic acids are capable of altering meristem development in plants. For example, an antisense construct of a clavata1 nucleic acid or a modified clavata1 nucleic acid is capable of altering the meristem development in plant tissue expressing the antisense or modified clavata1 nucleic acid. In addition, transformation with a clavata1 nucleic acid or modified nucleic acid can result in co-suppression of the endogeneous clavata1 alleles which in turn modifies the meristem development. Furthermore, clavata1 nucleic acids can be modified as described herein to produce modified clavata1 nucleic acids which when used to transform plant tissue result in varying degrees of meristem development in the tissues expressing the modified clavata1 nucleic acids.

As it is understood by those in the art, once the amino acid sequence of clavata1 is known, it is possible to generate a large number of nucleic acids which code for the clavata1 amino acid sequence, due to the degeneracy of the genetic code. Thus, for example, synthetic oligonucleotides may be made which use different codons than the naturally occurring plant codons. Such synthetic oligonucleotides can comprise the clavata1 nucleic acid or can be used to make or modify clavata1 nucleic acids.

The clavata1 proteins and nucleic acids of the invention are preferably recombinant. As used herein, “nucleic acid” may refer to either DNA or RNA, or molecules which contain both deoxy- and ribonucleotides. The nucleic acids include genomic DNA, cDNA, mRNA and oligonucleotides including sense and anti-sense nucleic acids. Such nucleic acids may also contain well known modifications in the ribose-phosphate backbone to increase stability and half life of such molecules in physiological environments.

Specifically included within the definition of nucleic acid are anti-sense clavata1 nucleic acids. Generally, anti-sense clavata1 nucleic acids function to prevent expression of mRNA encoding the clavata1 protein. That is, an anti-sense clavata1 nucleic acid such as an anti-sense RNA has a sequence complementary to all or part of the normal RNA transcript, such that anti-sense/sense hybrids are formed, which inhibit the synthesis of the endogeneous clavata1 protein. Thus, specifically included within the scope of the invention are the anti-sense or non-coding strands of the nucleic acid encoding the clavata1 proteins of the invention. It should be understood that it is not necessary that the anti-sense nucleic acid correspond to the full length sense strand, since generally only a stretch of anti-sense/sense hybridization is sufficient to inhibit translation. The hybridization conditions used for the determination of anti-sense hybridization will generally be high stringency conditions, such as 0.1XSSC at 65° C.

The nucleic acid may be double stranded, single stranded, or contain portions of both double stranded or single stranded sequence. By the term “recombinant nucleic acid” herein is meant nucleic acid, originally formed in vitro, in general, by the manipulation of nucleic acid by endonucleases, in a form not normally found in nature. Thus an isolated clavata1 nucleic acid, for example in a linear form, an expression vector formed in vitro by ligating DNA molecules that are not normally joined, an anti-sense construct, or a clavata1 nucleic acid, modified or wild-type, which is under the control of a heterologous promoter, are all considered recombinant for the purposes of this invention. Similarly, modified clavata1 nucleic acids are considered recombinant, whether isolated or reintroduced into the genome of a plant. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a “recombinant protein” is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. The protein may be modified. The definition includes a clavata1 protein from one organism produced in a different organism or host cell. A recombinant protein may be made at a significantly higher concentration than is normally seen, through the use of a inducible promoter or high expression promoter, such that the protein is made at increased concentration levels. For example, it is possible to introduce one or more copies of a modified clavata1 nucleic acid which, when expressed in the host plant, serves to interfere with the formation of functional multimeric clavata1 proteins. Alternatively, the protein may be made at significant lower concentrations than are normally seen. For example, it is possible to suppress the expression of endogeneous clavata1 proteins by transforming the plant with extra copies of the wild-type protein. Still further, the protein may be in a form not normally found in nature, as in the addition of an epitope tag or other label or in the amino acid substitution, insertion and deletion of one or more amino acid residue. Although not usually considered recombinant, the definition also includes proteins made synthetically.

Also included with the definition of clavata1 protein are clavata1 proteins from plants other than *Arabidopsis thaliana,* which are expressed from clavata1 nucleic acids as outlined below. As is known in the art, all or part of the clavata1 nucleic acid sequence of FIG. 5 (SEQ ID NO:1) may be used to clone and identify clavata1 nucleic acids from other plant species. For example, labelled probes corresponding to all or part of a known clavata1 nucleic acid (SEQ ID NO:1) can be used for in situ hybridization to detect the presence of a clavata1 gene in a particular plant species. Preferred probes are of the above identified unique clavata1 sequences. In addition, such probes can be used to screen genomic or cDNA libraries of a different plant species or to identify one or more bands containing all or part of a clavata1 gene by hybridization to an electrophoretically separated preparation of genomic DNA digested with one or more restriction endonucleases.

It should be understood that clavata1 genes from other plants may have one or more introns, similar to the clavata1 gene from Arabidopsis (see FIG. 5 (SEQ ID NO:1)).

Hybridization conditions will vary depending on the probe used. When a unique nucleotide sequence is used, such as the amino- or carboxy-terminal sequence or the LRR with the NBS, stringency conditions can vary from relatively high stringency to reduced stringency conditions. High stringency hybridization conditions are 0.1XSSPE at 65° C. Reduced stringency conditions are 2XSSPE at 50° C. When the hybridization probe covers a region which has a potentially lower sequence homology to known clavata1 nucleic acids, e.g. a region covering a portion of the leucine rich repeat or the kinase, moderate stringency conditions may be used, i.e. 0.1XSSPE at 50° C.

Using the BW4/KD4 probe (SEQ ID NO:8) and reduced stringency conditions, hybridization to alfalfa and maize was seen (data not shown). Since maize is only very distantly related to Arabidopsis, this probe is particularly useful to clone clavata1 nucleic acids from a variety of plant species.

In particular, clavata1 nucleic acids may be found in alfalfa, maize, rice, wheat, barley, tomato, and species of Brassicas (canola, cabbage, cauliflower, broccoli), in addition to the plants listed below.

Once the clavata1 nucleic acid is identified, it can be cloned and, if necessary, its constituent parts recombined to form the entire clavata1 nucleic acid. Once isolated from its natural source, e.g., contained within a plasmid or other vector or excised therefrom as a linear nucleic acid segment, the clavata1 nucleic acid can be further used as a probe to identify and isolate other clavata1 nucleic acids as described above. It can also be used as a "precursor" nucleic acid to make modified clavata1 nucleic acids and proteins.

By the term "modified clavata1 nucleic acid" or "variant clavata1 nucleic acid" herein is meant a clavata1 nucleic acid containing a substitution, insertion or deletion of one or more nucleotides of the precursor clavata1 nucleic acid. It is to be understood that "modified" in this sense is relative to the starting sequence; that is, the precursor nucleic acid may be a naturally occurring clavata1 nucleic acid, or it may already have been modified one or more times. Thus, modified clavata1 nucleic acids have substitutions, insertions or deletions of nucleotides as compared to the precursor clavata1 nucleic acids. Thus, the naturally occurring clavata1 nucleic acid may be modified via site-directed mutagenesis, cassette mutagenesis, transposon mutagenesis, chemical mutagenesis, ionizing radiation or error-prone replication to yield a substitution, insertion or deletion of one or more nucleotides. In one embodiment, these modifications may not result in changes in the protein sequence; for example, unique restriction sites may be introduced or a particular codon bias created. Preferably however, these modifications result in a corresponding substitution, insertion or deletion in one or more amino acids encoded by the nucleic acid, and thus result in a modified clavata1 protein. For example, as outlined below, any amino acid may be substituted by any one of the other naturally occurring amino acids.

As for the nucleic acid, by the term "modified clavata1 protein" or "variant clavata1 protein" herein is meant a clavata1 protein containing a substitution, insertion or deletion of one or more amino acids of the precursor protein. It is to be understood that "modified" in this sense is relative to the starting sequence; that is, the precursor protein may be a naturally occurring clavata1 protein, or it may already have been modified one or more times. These variants fall into one or more of three classes: substitutional, insertional or deletional variants. These variants ordinarily are prepared by site specific mutagenesis of nucleotides in the DNA encoding the clavata1 protein, using cassette mutagenesis or other techniques well known in the art, to produce DNA encoding the variant, and thereafter expressing the DNA. However, just as for wild-type clavata1 proteins, variant clavata1 protein may be prepared by in vitro synthesis using established techniques, although currently these techniques are generally only used for the synthesis of fragments of about 100–150 amino acids. Amino acid sequence variants are characterized by the predetermined nature of the variation, a feature that generally sets them apart from naturally occurring allelic or interspecies variation of the clavata1 protein amino acid sequence. The variants typically exhibit the same qualitative biological activity as the naturally occurring analogue, although variants can also be selected which have modified characteristics.

Alternatively, a cloned precursor clavata1 nucleic acid can be systematically modified such that it encodes the substitution, insertion and/or deletion of one or more amino acid residues and tested to determine the effect of such modification on a plant's meristem development. These modifications may be made within the LRR domain, the transmembrane domain, or kinase domain. One method which may be used for identifying particular amino acid residues involved in clavata1 activity is the sequential substitution of the codons of a clavata1 nucleic acid with codons encoding a scanning amino acid such as glycine or alanine (See, e.g., PCT Publication W090/04788 published May 3, 1990) followed by transformation of each of the thus formed modified nucleic acids into a plant to determine the effect of such sequential substitution on the meristem development. Other approaches include random modifications or predetermined targeted modifications of the cloned clavata1 nucleic acid (See, e.g., PCT Publication No. W092/07090 published Apr. 30, 1992) followed by transformation of plant cells and the identification of progeny having an altered clavata1 phenotype. The clavata1 nucleic acid from those plants having the desired phenotype is isolated and sequenced to confirm or identify the modification responsible for the observed phenotype.

While the site or region for introducing an amino acid sequence variation is predetermined, the mutation per se need not be predetermined. For example, in order to optimize the performance of a mutation at a given site, random mutagenesis may be conducted at the target codon or region and the expressed clavata1 protein variants screened for the optimal combination of desired activity. Techniques for making substitution mutations at predetermined sites in DNA having a known sequence are well known, for example, M13 primer mutagenesis. Screening of the mutants is done using assays of clavata1 activities. For example, mutated clavata1 proteins may be tested biochemically, for example by assaying for kinase activity. Alternatively, the modified clavata1 proteins may be expressed in clavata1 null plants to evaluate biological activity. Also, clavata1 mutant can be generated using a large pool of transposon-insertion lines.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger, as when one of the functional domains is deleted. For example, the clv1-6 mutation of Arabidopsis is a frameshift, resulting in a deletion of the last 229 amino acids, replacing them with 19 novel amino acids.

Substitutions, deletions, insertions or any combination thereof may be used to arrive at a final derivative. Generally these changes are done on a few amino acids to minimize the alteration of the molecule. However, larger changes may be tolerated in certain circumstances.

There are a number of specific residues within the clavata1 protein which may be modified to alter the biological activity and phenotype of the clavata1 protein. In a preferred embodiment, the biological activity of the protein is decreased or eliminated, to allow for enlarged meristems.

For example, modifications may be made in the kinase domain. In particular, modifications may be made in the serine/theronine kinase consensus residues and in the tyrosine kinase consensus residues. The serine/theronine consensus residues include Gly699, Gly701, Val706, Ala718, Lys720, Glu737, Asp817, Lys819, Asn822, Asp835, Gly837, Pro863, Glu864, Asp877, Gly881, and Arg957 (Hanks et al., supra; see also FIG. 6). The consensus residues of tyrosine kinases include Gly699, Gly701, Gly704, Val706, Ala718, Lys720, Glu737, Gly772, Leu774, Gly801, His815, Arg816, Asp817, Asn822, Asp835, Phe836, Gly837, Glu864, Ser875, Asp876, Val877, Gly881, Glu886, Pro893, Pro935, Cys949, Arg957, and Pro958. These may be altered to substantially eliminate the kinase activity. One or more of these residues may be substituted with any one of the other 19 naturally occuring amino acids.

In a preferred embodiment, substitutions are made at positions corresponding to the clv1 series of mutations in Arabidopsis. As shown in the Examples, many of the clv1 mutants were sequenced and shown to have a variety of mutations in the clavata1 gene. Thus, when using genes from other plants, these clv1 mutations may be introduced into the clavata1 genes from other plants at positions that correspond or are equivalent to the Arabidopsis position. By "corresponding to" or "equivalent positions" herein is meant amino acid positions which may be determined by lining up the two sequences and determining the equivalent position in the other gene or amino acid sequence. An amino acid residue in a precursor clavata1 protein is equivalent to a particular residue in the clavata1 protein of *Arabidopsis thaliana* if it is homologous in position in either primary or tertiary structure to the specified residue of the Arabidopsis clavata1 protein.

In order to establish homology by way of primary structure, the primary amino acid sequence of a precursor clavata1 protein is directly compared by alignment with the primary sequence of the clavata1 *Arabidopsis thaliana* protein. Such alignment will take into account the potential insertion or deletion of one or more amino acid residues as between the two sequences so as to maximize the amino acid sequence homology. A comparison of a multiplicity of clavata1 protein sequences with that of *Arabidopsis thaliana* provides for the identification of conserved residues among such sequences which conservation is preferably maintained for further comparison of primary amino acid sequence. Based on the alignment of such sequences, the skilled artisan can readily identify equivalent residues. Such equivalent residues are selected for modifications analogous to those of other modified clavata1 proteins which confer the desired phenotype.

In addition to homology at the primary sequence level, equivalent residues can be identified based upon homology at the level of tertiary structure. The determination of equivalency at this level will generally require three-dimensional crystal structures for a clavata1 protein or modified clavata1 protein from Arabidopsis (or crystal structure of another clavata1 protein having defined equivalent resiudes) and the crystal structure of a selected clavata1 protein. Equivalent residues at the level of tertiary structure are defined as those for which the atomic coordinates of two or more of the main chain atoms of a particular amino acid residue of the selected clavata1 protein, as compared to the clavata1 protein from Arabidopsis, are within 0.13 nm and preferably 0.10 nm after alignment. Alignment is achieved after the best model has been oriented and positioned to give the maximum overlap of atomic coordinates of non-hydrogen protein atoms of the clavata1 proteins in question.

Preferred modifications are as follows. The clv1-1 and clv1-5 mutants in Arabidopsis have a G to A nucleotide base change at position 5015, resulting in an amino acid change from glycine to aspartic acid at amino acid residue 890. Based on the crystal structures of known kinases (kinase PKA, Zheng et al., Biochem. 32: 2154–2161 (1993), Bossemeyer et al., EMBO J. 12: 849–859 (1993); MAPK (Zhang et al., Nature 367: 704–711 (1994); and cdk2 (De Bondt et al., Nature 363: 595–602 (1993)), this residue is within the active site kinase domain, although it is not an active site residue. This results in a semi-dominant, intermediate severe phenotype. That is, while wild type Arabidopsis flowers have two fourth whorl carpels, the homozygotic clv1-1 and clv1-5 mutants have 4–5 carpels. In addition, heterozygous clv1-1 mutants have a small but significant increase in carpel number, thus reflecting a semi-dominant allele. Thus, in a preferred embodiment, clavata1 nucleic acids are modified to result in an amino acid substitution at a position corresponding to Gly890 in Arabidopsis; a particularly preferred substitution is to an Asp, although any of the other 18 amino acids may be used as well, with other large, charged residues like Glu, Arg and Lys being preferred.

Similarly, the clv1-2 mutant contains a G to A nucleotide change at position 5169, resulting in an amino acid change from glycine to glutamic acid at amino acid residue 881. As for the clv1-1 mutant, this residue is thought to be near the active site of the kinase domain but is not an active site residue. This results in a weak phenotype; that is, clv1-2 homozygotes in Arabidopsis have close to three carpels. Thus, in a preferred embodiment, clavata1 nucleic acids are modified to cause an amino acid substitution at a position corresponding to Gly881 in Arabidopsis; a particularly preferred substitution is to a Glu, although any of the other 18 amino acids may be used as well.

The clv1-4 mutant contains a G to A nucleotide change at position 3050, resulting in an amino acid change from glycine to glutamic acid at amino acid residue 201. This residue is within the LRR domain, and eliminates the NBS site. This results in the strongest phenotype so far identified; clv1-4 homozygotes in Arabidopsis have close to 6 carpels on average. Thus, in a preferred embodiment, clavata1 nucleic acids are modified to result in an amino acid substitution at a position corresponding to Gly201 in Arabidopsis; a particularly preferred substitution is to a Glu, although any of the other 18 amino acids may be used as well. In addition, the other residues of the NBS site may be altered, and in particular the other consensus NBS amino acid residues, namely Gly206, Lys207, and Ser208. Alternatively, deletion mutants may be made which delete all or part of the NBS site.

The clv1-6 mutant has an added A nucleotide in the codon for Arg751. The resulting frameshift eliminates almost the entire kinase domain and replaces it with 19 novel amino acids before encountering a stop codon. This was a surprising finding because the homozygotic clv1-6 has a weak phenotype, having roughly 3 carpels on average. This suggests that there is readthrough of this frameshift to provide for some of the correct protein, including the kinase domain. Alternatively, it is possible that removing the entire kinase domain has less of an effect on clavata1 function than slightly altering it, as in the intermediate alleles.

The clv1-8 mutant has a G to A nucleotide change at position 3331, resulting in an amino acid change from aspartic acid to asparagine at amino acid residue 295, also within the LRR receptor domain. This results in another strong phenotype; clv1-8 homozygotes in Arabidopsis have close to 6 carpels on average. Thus, in a preferred embodiment, clavata1 nucleic acids are modified to result in an amino acid substitution at a position corresponding to Asp295 in Arabidopsis; a particularly preferred substitution is to a Asn, although any of the other 18 amino acids may be used as well; for example, changes to positively charged residues, i.e. Lys and Arg may be done. In addtion, this area of the LRR receptor region may represent a ligand-binding region, and thus changes in nearby amino acids may also disrupt binding of the ligand.

The clv1-9 mutant has a C to T nucleotide change at position 4964, resulting in an amino acid change from alanine to valine at amino acid residue 839, also putatively near the active site of the kinase domain. This results in another weak phenotype; clv1-9 homozygotes in Arabidopsis have close to 3 carpels on average. Thus, in a preferred embodiment, clavata1 nucleic acids are modified to result in an amino acid substitution at a position corresponding to Ala839 in Arabidopsis; a particularly preferred substitution is to a Val, although any of the other 18 amino acids may be used as well.

Sequencing of other clv1 mutants in Arabidopsis will suggest other mutations as well.

Once a clavata1 nucleic acid or modified clavata1 nucleic acid is made or isolated, it can be used to construct vectors for transforming plant cells. The construction of such vectors is facilitated by the use of a shuttle vector which is capable of manipulation and selection in both plant and a convenient cloning host such as a prokaryote. Such shuttle vectors thus can include an antibiotic resistance gene for selection in plant cells (e.g. kanamycin resistance) and an antibiotic resistance gene for selection in a bacterial host (e.g. actinomycin resistance). Such shuttle vectors also contain an origin of replication appropriate for the prokaryotic host used and preferably at least one unique restriction site or polylinker containing unique restriction sites to facilitate vector construction. Examples of such shuttle vectors include pMON530 (Rogers et al., Methods in Enzymology 153: 253–277 (1988)) and pCGN1547 (McBride et al., Plant Molecular Biol. 14: 269–276 (1990)).

In a preferred embodiment, a promoter is linked to the nucleic acid encoding the clavata1 protein to drive expression of the nucleic acid within at least a portion of the tissues of a transformed plant. Such promoters may be obtained from plants, plant pathogenic bacteria or plant viruses. Constitutive promoters include the 35S and 19S promoters of cauliflower mosaic virus (CaMV35S and CaMV19S), the full-length transcript promoter from the Figwort mosaic virus (FMV35S) (See PCT Publication No. WO92/12249 published Jul. 23, 1992) and promoters associated with Agrobacterium genes such as nopaline synthase (NOS), mannopine synthase (MOS) or octopine synthase (OCS). Other constitutive promoters include the alpha-1 and beta-1 tubuline promoters (Silflow et al., Devel. Genet. 8: 435–473 (1987)), the histone promoters (Chaubet, Devel. Genet. 8: 461–473 (1987)) and the promoters which regulate transcription of clavata1 nucleic acids.

In some embodiments, temporal specific promoters can be used to control expression of clavata1 and modified clavata1 nucleic acids. Fruit and floral meristem promoters are particularly useful for antisense constructions. Examples of fruit specific promoters include the E8, E4, E17 and J49 promoters from tomato (Lincoln et al., Mol. Gen. Genet. 212: 71–75 (1988)) and the 2A11, Z130 and Z70 promoters from tomato as described in U.S. Pat. Nos. 4,943,674, 5,175,095 and 5,177,307.] In addition, preferential expression in rapidly dividing tissue can be obtained utilizing the plant EF-1-alpha promoter as described in U.S. Pat. No. 5,177,011. Examples of floral specific promoters include AP1, the leafy promoter and promoters from the apetala, pistillata and agamous genes. A promoter system for targetting expression in the leaves of a transformed plant is a chimeric promoter comprising the CaMV35S promoter ligated to the portion of the ssRUBISCO gene which represses the expression of ssRUBISCO in the absence of light. In addition, pollen-specific promoters can also be used. Such promoters are well known to those skilled in the art and are readily available. An example of such a promoter is Zn13 (Hamilton et al, Plant Mol. Biol. 18: 211–218 (1992)). This promoter was cloned from corn (monocot) but functions as a strong and pollen-specific promoter when used in tobacco (dicot).

Examples of inducible promoters which can be used for conditional expression of clavata1 nucleic acids include those from heat-shock protein genes such as the PHS1 heat shock protein gene (Takahashi et al., Mol. Gen. Genet. 219: 365–372 (1989)) and light-inducible promoters including the three chlorophyll a/b light harvesting protein promoters (Leutwiler et al., Nucl. Acid Res. 14: 4051–4064 (1986)) and the pre-ferredoxin promoter (Vorst et al. Plant Mol. Biol. 14: 491–499 (1990)).

Other preferred promoters include the promoter from the 27 kD subunit of the glutathione-S-transferase, isoform II (GST-II-27). This promoter is induced by chemical compounds known as "herbicide safeners", which can be applied, for example sprayed, onto the plants to induce the promoter. See PCT/GB92/01187 and PCT/GB90/00101, expressly incorporated herein. This promoter functions in both monocotyledons and dicotyledons. Similarly, PCT/GB90/00115, expressly incorporated herein, describes pseudo-operator sequences for use in expressing foreign genes. PCT/GB93/00764, also expressly incorporated herein, describes chemically-inducible gene expression cassettes which can use the alcA/alcR gene activation system of *Aspergillus nidulans.*

The vectors of the invention are designed such that the promoter sequence contained in the vector or the promoter targeted in the plant cell genome as described below are operably linked to the nucleic acid encoding the clavata1 or modified clavata1 nucleic acid. When the positive strand of the clavata1 nucleic acid is used, the term "operably linked" means that the promoter sequence is positioned relative to the coding sequence of the clavata1 nucleic acid such that the RNA polymerase is capable of initiating transcription of the clavata1 nucleic acid from the promoter sequence. In such embodiments it is also preferred to provide appropriate ribosome binding sites, transcription initiation and termination sequences, translation initiation and termination sequences and polyadenylation sequences to produce a functional RNA transcript which can be translated into clavata1 protein. When an antisense orientation of the clavata1 nucleic acid is used as described below, all that is required is that the promoter be operably linked to transcribe the clavata1 antisense strand. Thus, in such embodiments, only transcription start and termination sequences are need to provide an RNA transcript capable of hybridizing with the mRNA or other RNA transcript from an endogeneous clavata1 gene or modified clavata1 nucleic acid contained within a transformed plant cell. In addition to promoters, other expression regulation sequences, such as enhancers, can be added to the vector to facilitate the expression of clavata1 nucleic acid in vivo.

In a further embodiment of the invention, the vector used to transform plant cells is constructed to target the insertion of the clavata1 nucleic acid into an endogeneous promoter within a plant cell. One type of vector that can be used to target the integration of a modified clavata1 nucleic acid to an endogenous promoter comprises a positive-negative selection vector analogous to that set forth by Monsour et al., Nature 336: 348–352 (1988) which describes the targeting of exogenous DNA to a predetermined endogenous locus in mammalian ES cells. Similar constructs utilizing positive and negative selection markers functional in plant cells can be readily designed based upon the identification of the endogenous plant promoter and the sequence surrounding it. When such an approach is used, it is preferred that a replacement-type vector be used to minimize the likelihood of reversion to the wild-type genotype.

Similarly, homologous recombination vectors can be designed to replace the endogenous copy or copies of the clavata1 gene with a modified clavata1 nucleic acid. For example, vectors are readily designed based on the sequence of the endogeneous clavata1 nucleic acid and the upstream and downstream sequences. In this way, the wild-type copy or copies of the gene within a plant may be replaced by a modified clavata1 nucleic acid that encodes a clavata1 protein exhibiting a modified clavata1 phenotype. For example, modified clavata1 nucleic acids which encode any of the amino acid substitutions outlined above may be used, or deletion mutants that delete a significant portion of the gene may be used.

In a further embodiment, vectors are designed to incorporate extra copies of a clavata1 or modified clavata1 nucleic acid into the genome of the plant as is known in the art. As outlined above, it appears that the clavata1 protein functions as a multimer, and that the incorporation of modified clavata1 proteins into the multimer is sufficient to alter, reduce or eliminate clavata1 function such that altered phenotypes are seen, presumably through interfering with proper multimer formation. This effect is presumably seen in the semi-dominant alleles of Arabidopsis such as clv1-1 and clv1-5. Accordingly, the wild-type phenotype may be "swamped out" by the addition of one or more copies of a modified clavata1 nucleic acid, thereby preferably resulting in enlarged meristems. Alternatively, it is a well known plant phonomenon that the addition of extra copies of wild-type genes may result in co-suppression of all copies of the gene, both endogeneous and exogeneous, resulting in enlarged meristems. In these embodiments, both inducible and constitutive promoters may be used.

In an additional embodiment, the expression of a clavata1 nucleic acid is in the antisense orientation to modulate meristem development by reduction in translation of the endogeneous clavata1 mRNA transcript, thus altering the clavata1 phenotype, preferably resulting in enlarged meristems. Similar to the sense constructs, antisense transcription can be controlled with constitutive or inducible promoters.

The clavata1 protein may also be made as a fusion protein, using techniques well known in the art. Thus, for example, for the creation of monoclonal antibodies, if the desired epitope is small, the clavata1 protein may be fused to a carrier protein to form an immunogen. Alternatively, the clavata1 protein may be made as a fusion protein to increase expression.

Once a vector is constructed, the transformation of plants can be carried out in accordance with the invention by essentially any of the various transformation methods known to those skilled in the art. Such methods are generally described in Methods and Enzymology, vol. 153 ("Recombinant DNA Part D"), 1987, Wu and Grossman, Academic Press, eds. As used herein, the term "transformation" means the alteration of the genotype of a plant cell by the introduction of exogenous nucleic acid. Particular methods for transformation of plant cells include the direct microinjection of nucleic acid into a plant cell by use of micropipettes. Alternatively, the nucleic acid can be transferred into a plant cell by using polyethylene glycol (Paszkowski et al. *EMBO J.* 3: 2717–2722 (1984)). Other transformation methods include electroporation of protoplasts (Fromm, et al. *Proc. Natl. Acad. Sci. U.S.A.* 82: 5824 (1985); infection with a plant specific virus, e.g., cauliflower mosaic virus (Hohn et al. "Molecular Biology of Plant Tumors", Academic Press, New York (1982), pp. 549–560) or use of transformation sequences from plant specific bacteria such as *Agrobacterium tumefaciens,* e.g., a Ti plasmid transmitted to a plant cell upon infection by *agrobacterium tumefaciens* (Horsch et al. *Science* 233: 496–498 (1984); Fraley et al. *Proc. Natl. Acad. Sci. U.S.A.* 80: 4803 (1983)). Alternatively, plant cells can be transformed by introduction of nucleic acid contained within the matrix or on the surface of small beads or particles by way of high velocity ballistic penetration of the plant cell (Klein et al. *Nature* 327: 70–73 (1987)).

After the vector is introduced into a plant cell, selection for successful transformation is typically carried out prior to regeneration of a plant. Such selection for transformation is not necessary, but facilitates the selection of regenerated plants having the desired phenotype by reducing wild-type background. Such selection is conveniently based upon the antibiotic resistance and/or herbicide resistance genes which may be incorporated into the transformation vector.

Practically all plants can be regenerated from cultured cells or tissues. As used herein, the term "regeneration" refers to growing a whole plant from a plant cell, a group of plant cells or a plant part. The methods for plant regeneration are well known to those skilled in the art. For example, regeneration from cultured protoplasts is described by Evans et al. "Protoplasts Isolation and Culture", *Handbook of Plant Cell Cultures* 1: 124–176 (MacMillan Publishing Co., New York (1983); M. R. Davey, "Recent Developments in the Culture and Regeneration of Plant Protoplasts", *Protoplasts* (1983) *Lecture Proceedings,* pp. 12–29 (Birkhauser, Basil 1983); and H. Binding "Regeneration of Plants", *Plant Protoplasts,* pp. 21–73 (CRC Press, Bocaraton 1985). When transformation is of an organ part, regeneration can be from the plant callus, explants, organs or parts. Such methods for regeneration are also known to those skilled in the art. See, e.g., *Methods in Enzymology,* supra.; *Methods in Enzymology,* Vol. 118; and Klee et al. *Annual Review of Plant Physiology* 38: 467–486.

A preferred method for transforming and regenerating petunia with the vectors of the invention is described by Horsch, R. B. et al. (1985) *Science* 227: 1229–1231. A preferred method for transforming cotton with the vectors of the invention and regenerating plants therefrom is described by Trolinder et al. (1987) *Plant Cell Reports* 6: 231–234. Tomato plant cells are preferably transformed utilizing Agrobacterium strains by the method as described in McCormick et al., *Plant Cell Reports* 5: 81–84 (1986).

Once plants have been regenerated, one or more plants are selected based upon a change in the clavata1 phenotype. Generally, this will involve a visual inspection of the plants for enlarged floral and apical shoot meristems, an increase in the number of leaves and flowers, an increase in fruit size and seed number, fasciation, and increased inflorescence. For example, shoot apical meristems may become enlarged, leading to fasciation or cresting, causing the stem to become straplike, with an increase in the number of leaves and flowers. In the floral meristems, the enlargement leads to an increase in the number of floral organs, including an increase in carpel number, which increases fruit size and seed number. When a tissue and/or temporal-specific promoter is used, the determination of a modulation in the clavata1 phenotype is determined in the appropriate tissue at the appropriate time and if necessary under the appropriate conditions to acitvate/inactivate an inducible promoter. In each case, the clavata1 phenotype is preferably compared to the same phenotype in a wild-type plant. Transformants can also be identified by PCR analysis. A set of primers specific for the transformed DNA can be used on a small amount of plant material (less than 1 leaf) to identify true transformants.

The plants may be grown, and seeds collected, as is known in the art.

The following are particularly prefered embodiments for modulating clavata1 phenotype in plants.

In one embodiment, a modified clavata1 nucleic acid is linked to a constitutive or inducible promoter and used in the construction of homologous recombination vectors. The homologous recombinantion sequences may be coding sequences or 3' and 5' flanking regions, as is known in the art. In this way it is possible to replace the endogenous wild-type clavata1 sequences with modified clavata1 sequences. Preferred embodiments utilize modified clavata1 sequences which encode amino acid changes at positions equivalent to Gly-890, Gly-881, Ala-839, Gly-201, Asp-295, Gly-206, Lys-207, and Ser-208 in the clavata1 protein from *Arabidopsis thaliana* (SEQ ID NO:2). In a preferred embodiment, the plants are transformed and bred to be homozygotic for the mutation or mutations. Alternatively, when the mutation is dominant or semi-dominant, that is it exhibits an altered clavata1 phenotype as a heterozygote, the plants may be heterozygotes.

In an alternative embodiment, plants may be transformed with vectors containing constitutive or inducible promoters linked to modified clavata1 nucleic acids wherein the endogenous wild-type clavata1 gene remains intact. Such vectors are generally inserted at random sites in the plant genome. Without being bound by theory, it appears that this results in altered clavata1 phenotypes as a result of one or two possible mechanisms. As outlined above, the clavata1 protein may act as a multimer; incorporating mutant clavata1 subunits may attenuate the wild-type activity. Alternatively, the expression of modified clavata1 nucleic acids may co-suppress the expression of the wild-type nucleic acid. Thus, a preferred embodiment utilizes at least one, and preferably several, copies of a modified clavata1 nucleic acid integrated into the genome of a plant containing endogenous wild-type clavata1 nucleic acids.

In a similar preferred embodiment, plants may be transformed with vectors containing constitutive or inducible promoters linked to wild-type clavata1 nucleic acids wherein said vectors are randomly integrated such that the endogeneous wild-type clavata1 genes are unaffected. It is a well known plant phenomenon that these types of constructions result in the co-suppression of both the endogeneous and exogeneous copies of the gene.

In a preferred embodiment, antisense clavata1 nucleic acids are linked to inducible or constitutive promoters and are integrated into the genome of a plant using techniques known in the art. Thus, the antisense strand or non-coding strand of the clavata1 nucleic acid is expressed in plants. This results in antisense mRNA which hybridizes to the mRNA from the coding strand, and thus decreases or eliminates the expression of clavata1 protein. Accordingly, the levels of endogeneous clavata1 protein are decreased, resulting in an altered clavata1 phenotype, preferably enlargement of meristems.

In another embodiment, the clavata1 nucleic acids of the invention are used to make homologous recombinantion deletion vectors. That is, some or all of the coding region is deleted from the vector, and 3' and 5' flanking regions are used to allow homologous recombination. Preferably, all of the coding region is deleted, and flanking regions upstream and downstream from the coding region are used for the recombination, to minimize the chances of reversion to wild-type.

The invention can be practiced in a wide variety of plants to obtain useful phenotypes in both agricultural and horticultural plants. Agricultural uses are quite widespread. For example, the intermediate phenotype expressed by clv1-1 Arabidopsis (SEQ ID NO: 1) variants leads to 50% more leaves over the same period of time as wild-type plants. In addition, the flowers of clv1-1 variants develop twice as many seed-bearing carpels as wild-type plants, with a similar increase in stamen, petal and sepal number. These effects may be even greater for other mutations, such as seen in clv1-4 and clv1-8 in Arabidopsis. Thus, it is possible to increase the number of leaves, flowers, seeds and fruit of a plant, using the methods of the invention, especially in plants other than Arabidopsis.

For example, it is desirable to lower clavata1 activity in crops, leading to the generation of additional leaves before flowering begins. These additional leaves could act to provide greater energy production by the plant, increasing yield. The number of seed-bearing carpels could be increased, allowing for the production of additional seeds per plant.

Particularly suitable plants include tomato, banana, kiwi fruit, avocado, melon, mango, papaya, apple, peach and other climacteric fruit plants. Non-climacteric species from which clavata1 nucleic acids can be isolated include strawberry, raspberry, blackberry, blueberry, lettuce, cabbage, cauliflower, onion, broccoli, brussel sprout, cotton, canola, grape, soybean and oil seed rape. In addition, clavata1 nucleic acids can be isolated from flowering plants within the Division Magnoliophyta which comprise the angiosperms which include dicotyledons (Class Magnoliopsida and Dicotyledoneae) and monocotyledons (Class Liliopsida). Particularly preferred Orders of angiosperm according to "Taxonomy of Flowering Plants", by A. M. Johnson, The Century Co., NY, 1931 include Rosales, Cucurbitales, Rubiales, Campanulatae, Contortae, Tubiflorae, Plantaginales, Ericales, Primulales, Ebenales, Diapensiales, Prinulales, Pluinbaginales, Opuntiales, Parietales, Myritiflorae, Unibelliflorae, Geraniales, Sapindales, Rhamnales, Malvales, Pandales, Rhoendales, Sarraceniales, Ramales, Centrospermae, Santalales, Euphorbiales, Capparales, Aristolochiales, Julianiales, Juglandales, Fagales, Urticales, Myricales, Polygonales, Batidales, Balanopsidales, Proteales, Salicales, Leitneriales, Garryales, Verticillatae and Piperales. Particularly preferred plants include lily, carnation, chrysanthemum, petunia, rose, geranium, violet, gladioli, orchid, lilac, crabapple, sweetgum, maple, poinsettia, locust, ash and linden tree. These plants may serve as the source of clavata1 nucleic acids, and also as the recipients of modified or recombinant clavata1 nucleic acids.

Crops for which increased leaves are particular useful include leaf crops such as all types of lettuce, spinach, cabbage, brussel sprout, broccoli, and tobacco.

In some embodiments, the enlarged meristems of modified clavata1 plants results in thicker stems of the plants. This may be useful for preventing crop lodging, increasing wind resistance of plants and facilitating harvesting of certain plants. It may also be useful in the lumber industry and in other commercial tree crops.

The enlarged meristems of modified clavata1 plants also results in increased numbers of seeds. This is important for the seed industry as well as food seeds. For example, crops for which increased seeds are particularly useful include oil seeds such as canola, peanut, olive, rapeseed, sunflower, sesame and mustards. For the seed industry, crops such as tomatoe, maize, rice, wheat, barley, and others may be altered.

The enlarged meristems of modified clavata1 plants also results in alteration of the fruit of plants, both size and shape of fruit as well as number of fruit per plant. Crops for which this may be particularly important include tomato, banana, kiwi fruit, avocado, melon, mango, papaya, apple, peach, soybean, grape, berries, citrus crops, and plum.

Increased fruit may result from increased numbers of flowers. In addition, horticultural crops for which increased flowers are particularly useful include roses, carnations, and orchids.

In addition to providing a source for clavata1 nucleic acids which can be modified or isolated according to the teachings herein, the foregoing plants can be used as recipients of the modified nucleic acid to produce chimeric or transgenic plants which exhibit modified meristem development.

The clavata1 proteins of the invention are also useful to generate antibodies to the clavata1 protein. The antibodies have a variety of uses, including coupling to affinity chromotagraphy columns for the purification of clavata1 proteins, quantifying clavata1 protein at different stages of plant development, possibly activating the clavata1 protein by substituting for ligand binding and other uses apparent to those in the art.

In an additional embodiment, the clavata1 proteins are used to screen for antagonists and agonists of clavata1. Without being bound by theory, clavata1 most likely functions in signal transduction. Its structure, with an extracellular receptor domain and an intracellular kinase domain is similar to all known receptor tyrosine and serine/threonine kinases that control many aspects of animal development. The LRR domain presumably binds to a specific ligand, activating the kinase domain, perhaps through autophosphorylation as do many receptor kinases. Alternatively, it is possible that it is the absence of the ligand which is the signal. The activated kinase domain would then tranduct the signal by phosphorylating other protein targets. Clavata1 may allow extracellular signals to control the differentiation of cells at the shoot and floral meristem. Because clavata1 is a transmembrane receptor-kinase, manipulating the activity of clavata1 may be the most effective way to manipulate the signaling of this pathway. Regardless of whether there are multiple or competing ligands or multiple targets for the clavata1 kinase domain, all signaling would be transmitted through clavata1. Thus activating clavata1 would activate all of the necessary downstream signaling components and bypass any problems with multiple or competing signals. Similarly, inactivating clavata1 would break the link between any extracellular signals and cytoplasmic components, eliminating signaling. Accordingly, because clavata1 contains an extracellular receptor domain, it is uniquely positioned within the signaling pathway to be potentially controlled without the need for employing transgenic plants. For example, chemical antagonists could be sprayed on a field to inactivate clavata1, resulting in enlarged meristems and the resulting effects.

Thus, the clavata1 protein, and particularly the receptor domain, is used to screen for chemical agents that act as agonists or antagonists. Agonists, or activating agents would functionally bind to the clavata1 receptor, thereby activating the kinase domain. Antagonists would compete with the normal ligand for clavata1 receptor sites, serving as inhibitors of sorts. Antagonists may bind in a non-functional manner, perhaps by not promoting clavata1 multimerization, a process implicated in the activation of several receptor-kinases. In a preferred embodiment, clavata1 proteins are used to screen for potential antagonists, since antagonists would inhibit clavata1 activity and thus result in enlarged meristems. In a further embodiment, clavata1 proteins are used to screen for agonists, since combinations of antagonists and agonists are used to precisely control meristem development during the lifetime of a plant. For example, it may be desirable to have large meristems during early plant growth to increase leaves and flowers, but to inactivate clavata1 activity at later times to focus the plant's energy into fruit development.

Thus, in a preferred embodiment, the clavata1 proteins are used to screen for antagonists and agonists. The clavata1 proteins may be used in a variety of systems which are used to evaluate protein-protein interactions to identify suitable agents. For example, protein ligands which bind to the extracellular LRR domain of clavata1 can be identified by use of a two-hybrid vector system described in Fields et al., Nature 340: 245, and available commercially (Stratagene). In this system the clavata1 LRR domian is cloned in the vector pGB-4 such that it forms a hybrid with the yeast GAL4 DNA binding domain. A second vector, pGAD-Rx, is used to create a library of cDNAs from cells known to be expressing the protein ligand which binds the extracellular LRR domain of clavata1 (or alternatively, libraries of oligopeptides). The source of the cells expressing the protein ligand and thus mRNA substrate for cDNA synthesis may be wild-type meristems or enlarged meristems from a clavata1 mutant. Alternatively if it is absence of ligand which is the signal then cells from other tissues may be used as a source of DNA. Cloning of the library of cDNA inserts is done such that the inserts have a unidirectional insertion and that the expressed protein product is fused to the yeast GAL4 activation domain. The cDNA library of hybrid proteins (in pGAD-Rx) and the target LRR hybrid (in pGB-4) are co-expressed in yeast and the resulting recombinant clones assayed for transcriptional activation of the reporter gene. Reporter gene activity only occurs where the GAL4 activation domain forms a hybrid with the protein ligand that binds the LRR of clavata1 which in turn is fused to the GAL4 DNA binding domain. This protein-protein interaction prodcues a functional GAL4 transcriptional activator which recognizes and activates a GAL4 promoter fused to the 13-galactosidase reporter gene. Secondary screening is used to determine the deduced amino acid sequence and identity of the protein ligand. An addition screen for protein-protein interactions is Stone et al., Science (1994) 266: 793–795. Heterlologus expression of the plant gene in bacterial or yeast cells can then be used to produce large quantities of the protein ligand for further tests. In this manner, the clavata1 protein is used to identify a variety of proteins, including proteins which may bind to the clavata1 protein but which do not activate it.

A bioassay for clavata1 activation can be established by heterologous expression of the clavata1 gene in yeast cells such that the receptor kinase is correctly expressed and inserted into the yeast cellular membrane. Activation of the clavata1 receptor kinase is monitored via autophosphorylation of tyrosine, serine or threonine residues following bonding of ligand to the receptor. As noted above it is a common feature of transmembrane receptors that ligand binding results in autophosphorylation (in this case, tyrosine, serine and/or threonine residues) and dimerization of the receptor. In the bioassay, autophosphorylation of the receptor is detected through the use of antiphosphotyrosine monoclonal antibody (Cohen et al., PNAS 87: 4458 (199)); Kanakura et al., J. Biol. Chem. 266: 490 (1991)) in a whole cell ELISA test using the natural protein ligand isolated as described above as the postive control. Antiphosphotyrosine monoclonal antiserum is available commercially from Upstate Biotech, Inc. Once established such a bioassay for ligand binding can be automated and used to screen large chemical libraries for alternative, nonproteinaceous agonists. Alternatively the bioassay may be used to screen for antagonists which prevent the natural protein ligand binding to the receptor. In this case, the bioassay would detect a loss of ELISA signal.

Alternatively, after identifying the clavata1 ligand, plants may be regenerated in tissue culture from callus. Addition of exogeneous ligand to callus prevents meristem formation and thus no plants would regenerate. Random peptides and/or chemical agents could be added to antagonize the effect of the exogeneously added ligand, with successful antagonists allowing for plant regeneration.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLE

Cloning of the CLAVATA1 Locus from *Arabidopsis thaliana*

The CLAVATA 1 (CLV1) gene (SEQ ID NO:1) was isolated by undertaking a chromosome walk. This technique makes use of the existing genetic map and relies heavily on restriction fragment length polymorphisms (RFLP) between two different ecotypes of the *Arabidopsis thaliana* species. The CLV1 gene (SEQ ID NO:1) had previously been mapped to the bottom of chromosome 1 (FIG. 1; Koornneef et al., (1983) J. Hered. 74, 265–272). To generate meiotic recombination breakpoints near CLV1 (SEQ ID NO:1), two mapping crosses were made. Double mutants were first constructed between clv1-1 and flanking scorable markers ap1-1 and ga2. ap1-1 mutants have a visible flower phenotype that does not interfere with the clv1-1 floral phenotype. ga2 mutants lack gibberellic acid synthesis and, in the absence of exogenously applied gibberellic acid, will grow as dark green dwarf plants with aborted floral organs. Like clv1-1, the ap1-1 and ga2 mutants are both in the Landsberg-erecta (L-er) ecotype. Each resulting double mutant, clv1-1 ap1-1 and clv1-1 ga2, was crossed to a plant, wild-type at each locus, of the Columbia (Col-O) ecotype. The resulting F1 progeny were allowed to self. By selecting individual F2's that were only single mutants (i.e. clv1-1 or ga2 or ap1-1) recombination breakpoint in the regions adjacent to CLV1 (SEQ ID NO:1) were selected. In the 10 cM region between CLV1 (SEQ ID NO:1) and AP1, a total of 124 recombinant progeny were identified. In the 8 cM region between CLV1 (SEQ ID NO:1) and GA2, 82 recombinant progeny were scored. The mapping resolution is then about 1 break point per 0.1 cM or approximately one breakpoint every 20 kb on either side of CLV1 (SEQ ID NO:1).

Seeds were sown on a 1:1:1 mixture of soil:perlite:vermiculite saturated with a 1:200 dilution of Gnatrol (Abbott Laboratories) and 1:1000 dilution of Daconil fungicide (Chevron Ortho). Seeds were vernalized at 4° C. for four days then transferred to 25° C. under continuous light. Plants were fertilized once a week with 240 mg/L Plantex 20-20-20 (Plantco) and sprayed with a 1 to 50 dilution of Orthene insecticide (Chevron Ortho). Crosses were set up by emasculating the female parent and then hand pollinated with the male parent.

Each recombinant F2 was allowed to self, and genomic DNA was isolated from each F3 family separately. Total genomic DNA was isolated by grinding 2 g of plant tissue in 0.2M Tris (pH8), 0.1M EDTA, 1% N-lauroylsarcosine, 100 ug/ml proteinase K and ethanol precipitating twice. The final nucleic acid pellet was then resuspended in 4 ml of 1 g/ml CsCl with 1 mg ethidium bromide and centrifuged over night at 53K rpm in a Sorval Ultracentrifuge. The DNA band was pulled and the ethidium bromide was extracted with SSPE saturated isopropanol.

Genomic clones known to be polymorphic between the L-er and Col-O ecotypes were then mapped by hybridizing to Southern blots of the F3 DNA cut with the appropriate restriction enzymes (Chang et al., (1988) Proc. Natl. Acad. Sci. USA 85: 6856–6860 and Nam et al., (1989) Plant Cell 1: 699–705)). A total of four RFLP clones were mapped relative to CLV1 (SEQ ID NO:1) (FIG. 2). RFLP markers were mapped by digesting 3ug of genomic DNA with an appropriate restiriction enzyme as per manufacturers instructions. The DNA was then separated by agarose gel electrophoresis and transferred to a nylon membrane (Sambrook et al., 1989). The RFLP probe was then labelled using the Boehringer-Mannheim random prime labeling kit following the manufactures instructions. The Southern blot was then hybridized overnight at 65° C. in 6× SSPE, 5× Denhardt's reagent, 0.5% SDS and 100 ug/ml salmon sperm DNA. The filters were washed at 65° C. in 0.1X SSPE/0.1% SDS and then exposed to Kodak X-omat film overnight at −80° C. with an intensifying screen. YAC libraries, cosmid libraries and cDNA libraries were screened using the same conditions as above. All low stringency hybridizations were done at 65° C. in 6× SSPE, 5× Denhardt's reagent, 0.5% SDS and 100 ug/ml salmon sperm DNA, then washed at 50° C. in 2XSSPE/0.1% SDS.

Two clones (N7-24 and m532) mapped proximal to CLV1 (SEQ ID NO:1) and the other two clones (m237 and g6838) mapped distal to CLV1 (SEQ ID NO: 1). This fine scale mapping revealed that the order of the RFLP clones and their positions relative to CLV1 (SEQ ID NO:1) are different than previously reported (Hauge et. al., (1993) Plant Journal 3: 745–754)). Only one of the 124 recombination events between CLV1 (SEQ ID NO:1) and API was shown to lie between m532 and CLV1 (SEQ ID NO:1). This puts m532 approximately 16 kb away from the CLV1 gene (SEQ ID NO:1).

The two closest flanking RFLP clones, m532 and m237, were used to identify yeast artificial chromosomes (YACs) that contain CLV1 (SEQ ID NO:1). A single 180 kb YAC (D6; FIG. 2; Grill and Somerville, (1991) Mol. Gen. Genet. 226: 484–490) hybridized to both markers. This whole YAC was then used to screen a cosmid library (Olszewski et al., (1988) Nucl. Acid. Res. 16: 10765–10782). A total of 32 clones were isolated. These 32 clones were then probed with m532 and a single cosmid was isolated, called cosQ. This cosmid was then hybridized to the remaining 31 cosmids and three more cosmids were isolated, called cosR, cosT and cosY. Restriction enzymes were identified that give polymorphisms between L-er and Col-O for each of the cosmid clones. Each cosmid was then mapped using the F3 recombinants. CosR mapped 3 out of 124 recombinants proximal to CLV1 (SEQ ID NO:1). cosQ and cosY mapped 1 out of 124 proximal to CLV1 (SEQ ID NO:1) and cosT mapped 1 out of 82 distal to CLV1. Thus, the CLV1 gene (SEQ ID NO:1) must lie on cosQ, cosT or both (FIG. 3). Both cosmids were then transformed into clv1-4 mutant plants. Only cosT rescued the clv1 mutant phenotype indicating that the CLV1 (SEQ ID NO:1) was completely contained on cosT. A complete HindIII restriction map of cosT was generated and a single HindIII fragment was identified that contained the one distal recombination breakpoint previously identified (FIG. 4). This narrowed down the region of cosT that must contain the CLV1 gene (SEQ ID NO:1) to 12 kb.

The cosT HindIII restriction map was generated by digesting the cosmid with HindIII (New England Biolabs) following the manufacturers instructions and then analyzed by gel electrophoresis. The individual fragments were isolated and cloned into the HindIII site of the pGEM 7zf vector (Promega). Each subcloned fragment was sequenced using the USB Sequenase 7.0 kit. Oligonucleotides were then designed from both strands 100 to 200 bases into each fragment. Every primer combination was then used in a PCR reaction using intact cosT as the template. Primer combos that gave appropriately sized products represent adjacent restriction fragments. The fragments were then cloned into the TA cloning vector (Invitrogen) and seqeunced to verify their identity. The remainder of each cosT subclone was then sequenced by primer crawling.

This entire 12 kb genomic region was sequenced and two genes were identified, a potential receptor serine/threonine kinase and a ribosomal S18 protein (FIG. 4). Both genes were PCR amplified from seven different clv1 mutant alleles and sequenced to see if mutations could be identified in either gene. The ribosomal S18 gene and the LRR-kinase gene were PCR amplified from cosT and seven clv1 mutant alleles: clv1-1, clv1-2, clv1-4, clv1-5, clv1-6, clv1-8 and clv1-9 (Clark et al., 1993 and Leyser and Furner, 1992). The resulting PCR products were either cloned in the TA vector and sequenced or sequenced directly by a modified protocol using the USB Sequenase 7.0 kit. In short, the PCR products were isolated from a 0.8% LMP agarose gel. Sng of primer was annealed to approximately 500 ng of PCR product in the presence of 0.5% NP-40. The manufacturers instructions were then followed except that 0.5% NP-40 was added to the labelling mix.

No base changes were found in the S18 gene, but base changes were found in the receptor kinase gene in all seven clv1 allels (FIG. 5 (SEQ ID NOS:1 and 2) and FIG. 6 (SEQ ID NOS:3 and 4)). This provided definitive proof that the putative receptor kinase gene was the CLV1 gene (SEQ ID NO:1).

The CLV1 gene (SEQ ID NO:2) encodes a 980 amino acid protein with a predicted molecular weight of 107.7 kDa (FIG. 7). Comparing the genomic sequence to a partial cDNA clone, a single 79 base intron was identified near the 3' end of the open reading frame (FIG. 5 (SEQ ID NO:1)). The N-terminus of the protein contains a potential signal sequence followed by 21 complete leucine-rich repeats (LRRs). A LRR is a 23 to 24 amino acid motif with a consensus sequence of PXXLXXLXXLXXLXLXXNXXS-GXI (SEQ ID NO:9). LRR motifs are known to be involved in protein-protein interactions (Kobe and Deisenhofer, (1995) Nature. 374, 183–186), so the N-terminus of CLV1 (SEQ ID NO:1) may be an extracellular receptor. The fifth LRR contains the sequence GAGLSGKS (SEQ ID NO:10) which fits a consensus sequence for an ATP/GTP binding P-loop (GXXXXGKS/T (SEQ ID NO:11)). The clv1-4 mutation replaces the first G residue of this putative P-loop with an E residue. Following the LRRs is a run of 19 hydrophobic residues that may be a transmembrane domain. The putative cytoplasmic domain of the protein contains all the required residues for a protein serine/threonine kinase.

CLV1 ORF identification and translations were done using the MacVector program (Kodak IBI). Computer sequence analysis of the CLV1 gene product (SEQ ID NO:6) was accomplished using the Wisconsin GCG package on a VAX computer. Specifically, protein databases were searched using the BLAST program with all default parameters. Direct sequence alignments were done using the GAP or BESTFIT programs with a gap weight of 3.0 and a length weight of 0.10. Over 250 previously identified proteins showed sequence similarity to CLV1 (SEQ ID NO:6). These proteins fell into one of three general classes: LRR containing proteins, protein kinases and proteins with both LRR and kinase domains. The protein with the most sequence homology to CLV1 (SEQ ID NO:6) is another gene from *Arabidopsis thaliana* called RLK5 (SEQ ID NO:5) (FIG. 8; Walker, (1993) Plant Journal 3: 451–456). This gene (SEQ ID NO:5) was identified by low stringency hybridization with a maize serine/threonine kinase gene and contains 21 LRR in the N-terminal domain and all the consensus sequences of a serine/threonine kinase in the C-terminal domain. As yet, RLK5 (SEQ ID NO:5) has no known function in plant growth or development. CLV1 (SEQ ID NO:6) and RLK5 (SEQ ID NO:5) are 37% identical and 59% similar at the amino acid level and 51% identical at the nucleic acid level over the length of the whole gene. Other interesting proteins with sequence similarity to CLV1 include: Raf, S-receptor kinase genes, and a variety of plant pathogen resistance genes.

Low stringency hybridizations revealed the presence of at least one gene in the Arabidopsis genome with sequence homology to CLV1 (SEQ ID NO:1). In order to identify a CLV1 specific probe, various regions of the CLV1 gene (SEQ ID NO:1) were hybridized at low stringency to Southern blots containing total Arabidopsis DNA. Two regions of the gene were shown to be CLV1 specific. One such probe, called T11R1/R4 (SEQ ID NO:7), is 336 base pairs in length and spans 31 bases of the 5' untranslated region (UTR) and the first 305 bases. The second such gene specific probe, BW4/KD4 (SEQ ID NO:8) is 318 bases long and covers the last 301 bases and 17 bases of the 3' UTR (FIG. 9). The BW4/KD4 probe (SEQ ID NO:8) was used to probe a Southern blot containing alfalfa and maize genomic DNA at reduced stringency (2XSSPE at 50° C). Single cross hybridizing bands were detected in both alfalfa and maize so at least the BW4/KD4 gene specific probe (SEQ ID NO:8) may be useful for identifying CLV1 cognate homologs in a variety of plant species.

Without being bound by theory, one hypothesis for the action of the clavata1 gene (SEQ ID NO:1) and protein (SEQ ID NO:2) is based on the observation that the CLAVATA1 gene (SEQ ID NO:1) in Arabidopsis acts to regulate the amount of undifferentiated cells in both the shoot and floral meristem. In this model, there is a meristem-promoting activity (MPA) in shoot meristems and young flowers that maintains cells in a proliferative, undifferentiated state. CLAVATA1 (SEQ ID NO:2) may act to restrict this MPA to the center of the shoot meristem, so that cells on the flanks of the meristem can enter a specific developmental pathway. Similarly, in the young floral meristem there is a meristem-promoting activity (not necessarily the same MPA as in the shoot) that provides for floral meristem proliferation. This floral MPA is first restricted, then eliminated, by the action of the CLAVATA1 (SEQ ID NO:2) loci. In the clv1 mutant shoot meristem, high levels of MPA extend to the flanks of the shoot meristem, preventing these cells from entering a specific developmental pathway. Thus, the cells on the flanks of the soot meristem become part of the meristem, enlarging it. This is reiterated, leading to the 1000-fold larger clv1 mutant shoot meristem. In the young clv1 floral meristem, failure to properly restrict the MPA lead to a larger floral meristem because of additional meristem activity. As the flowers develop, the MPA is not eliminated from the floral meristem, so a pool of undifferentaited cells continues to proliferate throughout floral development.

A second possibility, which is not mutually exclusive with the above hypothesis, is that clavata1 protein (SEQ ID NO:2) acts as a "molecular switch" in cells of the shoot meristem. The protein might be present in all cells of the shoot meristem, and be responsible for detecting that the shoot apex has grown further away and/or that adjacent basal cells have begun to differentiate. This signal, perhaps transmitted via cell-to-cell communication, would allow the cells to enter a specific developmental pathway. Thus CLAVATA1 (SEQ ID NO:2) would act to promote the switch of cells from an undifferentiated toward a differentiated state in both the shoot and floral meristem.

We claim:

1. An isolated nucleic acid encoding a clavata1 protein.

2. The isolated nucleic acid of claim 1 comprising nucleic acid having a sequence at least 55% similar to that shown in FIG. 5 (SEQ ID NO:1).

3. The isolated nucleic acid of claim 1 comprising nucleic acid capable of hybridizing to the nucleic acid sequence shown in FIG. 5 (SEQ ID NO:1).

4. The isolated nucleic acid of claim 1 comprising nucleic acid that encodes the amino acid sequence shown in FIG. 5 (SEQ ID NO:2).

5. The isolated nucleic acid of claim 1 comprising nucleic acid having the sequence shown in FIG. 5 (SEQ ID NO: 1).

6. An expression vector comprising transcriptional and translational regulatory DNA operably linked to DNA encoding a clavata1 protein.

7. A plant cell transformed with an expression vector comprising a nucleic acid encoding a clavata1 protein.

8. The isolated nucleic acid of claim 1 comprising nucleic acid having a sequence at least 65% similar to that shown in FIG. 5 (SEQ ID NO:1).

9. The isolated nucleic acid of claim 1 comprising nucleic acid having a sequence at least 75% similar to that shown in FIG. 5 (SEQ ID NO: 1).

10. The isolated nucleic acid of claim 1 comprising nucleic acid encoding a clavata1 protein which is at least 45% similar to the protein shown in FIG. 5 (SEQ ID NO:2).

11. An expression vector according to claim 6 comprising transcriptional and translational regulatory DNA operably linked to the nucleic acid according to claim 2, 3, 4, 5, 8 or 9.

12. A plant cell transformed with the nucleic acid according to claim 1, 2, 3, 4, 5, 8, 9 or 10.

13. A plant comprising plant cells according to claim 12.

* * * * *